United States Patent
Capelli et al.

(10) Patent No.: US 9,675,544 B2
(45) Date of Patent: Jun. 13, 2017

(54) VOLATILE ANESTHETIC COMPOSITIONS COMPRISING EXTRACTIVE SOLVENTS FOR REGIONAL ANESTHESIA AND/OR PAIN RELIEF

(75) Inventors: Christopher C. Capelli, Houston, TX (US); Phillip C. Phan, Houston, TX (US); Allen W. Burton, Houston, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 432 days.

(21) Appl. No.: 12/863,755

(22) PCT Filed: Jan. 22, 2009

(86) PCT No.: PCT/US2009/031706
§ 371 (c)(1),
(2), (4) Date: Oct. 15, 2010

(87) PCT Pub. No.: WO2009/094459
PCT Pub. Date: Jul. 30, 2009

(65) Prior Publication Data
US 2011/0039944 A1 Feb. 17, 2011

Related U.S. Application Data

(60) Provisional application No. 61/022,665, filed on Jan. 22, 2008.

(51) Int. Cl.
| | | |
|---|---|---|
| *A61K 9/00* | (2006.01) | |
| *A61K 31/02* | (2006.01) | |
| *A61K 31/08* | (2006.01) | |
| *A61K 47/20* | (2006.01) | |
| *A61K 47/22* | (2006.01) | |
| *A61K 9/107* | (2006.01) | |
| *A61K 9/127* | (2006.01) | |

(52) U.S. Cl.
CPC .......... *A61K 9/0014* (2013.01); *A61K 9/0019* (2013.01); *A61K 9/0085* (2013.01); *A61K 31/02* (2013.01); *A61K 31/08* (2013.01); *A61K 47/20* (2013.01); *A61K 47/22* (2013.01); *A61K 9/107* (2013.01); *A61K 9/127* (2013.01)

(58) Field of Classification Search
CPC ...... A61K 31/02; A61K 31/08; A61K 9/0014; A61K 9/0019; A61K 9/0085; A61K 9/107; A61K 9/127; A61K 47/20; A61K 47/22

See application file for complete search history.

(56) References Cited

U.S. PATENT DOCUMENTS

| | | | |
|---|---|---|---|
| 3,097,133 A | 7/1963 | Suckling et al. | 604/512 |
| 3,720,587 A | 3/1973 | Croix | 203/58 |
| 4,109,651 A | 8/1978 | Steigerwald | 128/145.8 |
| 4,453,951 A | 6/1984 | Ohno | 51/307 |
| 4,622,219 A | 11/1986 | Haynes | 424/38 |
| 4,744,989 A | 5/1988 | Payne et al. | 424/490 |
| 4,794,921 A | 1/1989 | Lindkvist | 128/203.29 |
| 4,879,062 A | 11/1989 | Moore | 252/315.1 |
| 4,954,487 A * | 9/1990 | Cooper et al. | 514/159 |
| 4,994,025 A | 2/1991 | DeAntonio et al. | 604/28 |
| 5,114,714 A | 5/1992 | Young et al. | 424/400 |
| 5,230,778 A | 7/1993 | Gavlin et al. | 203/58 |
| 5,235,971 A | 8/1993 | Falb et al. | 128/203.14 |
| 5,336,429 A | 8/1994 | Barthelemy et al. | 252/171 |
| 5,466,468 A | 11/1995 | Schneider et al. | 424/450 |
| 5,552,404 A | 9/1996 | Chang et al. | 514/255.04 |
| 5,563,153 A * | 10/1996 | Mueller et al. | 514/305 |
| 5,568,910 A | 10/1996 | Koehler et al. | 251/83 |
| 5,677,290 A | 10/1997 | Fukunaga | 514/46 |
| 5,679,650 A | 10/1997 | Fukunaga et al. | 514/46 |
| 5,690,968 A | 11/1997 | Ross et al. | 424/718 |
| 5,854,249 A | 12/1998 | Chang et al. | 514/252.13 |
| 5,874,469 A | 2/1999 | Maniar et al. | 514/550 |
| 5,919,826 A | 7/1999 | Caruso | 514/629 |
| 5,942,497 A | 8/1999 | Fukunaga et al. | 514/46 |
| 5,976,072 A | 11/1999 | Greenberg | 600/120 |
| 6,248,788 B1 | 6/2001 | Robbins et al. | 514/627 |

(Continued)

FOREIGN PATENT DOCUMENTS

| | | |
|---|---|---|
| EP | 0 711 289 | 8/2000 |
| GB | 445289 | 4/1936 |

(Continued)

OTHER PUBLICATIONS

Remington: The Science and Practice of Pharmacy, 2005, Lippincott Williams and Wilkins, 21st ed., pp. 871-876.*
Physical property information for isoflurane, International Programme on Chemical Safety, validated 2002.*
Gordon et. al., Journal of Neurosurgery, 1995, vol. 83, pp. 875-877.*
Fassoulaki et al., "Skin application of isoflurane attenuates the responses to a mechanical and an electrical stimulation," *Can. J. Anaesth.*, 45(12):1151-1155, 1998.
Fassoulaki et al., "Local application of volatile anesthetics attenuates the response to a mechanical stimulus in humans," *Can. J. Anesth.*, 52(9):951-957, 2005.
Fassoulaki et al., "Percutaneous loss of desflurane, isoflurane, and halothane in humans," *Anesthesiology*, 74(3):479-483, 1991.
Skouteri et al., "Local application of halothane, isoflurane or sevoflurane increases the response to an electrical stimulus in humans," *Acata Anaesthesiol. Belg.*, 58(3):169-75, 2007.

(Continued)

*Primary Examiner* — Sarah Pihonak
(74) *Attorney, Agent, or Firm* — Parker Highlander PLLC

(57) ABSTRACT

The present invention provides methods for reducing pain in a subject in need of such pain reduction by delivering, e.g., intrathecally or epidurally, a volatile anesthetic dissolved in a solution comprising an extractive solvent, e.g., DMSO or NMP, in an amount effective to reduce pain. Chronic or acute pain may be treated, or the anesthetic may be delivered as a regional anesthesia to a subject to anesthetize a portion the subject prior to a surgery, hi certain embodiments, isoflurane, halothane, enflurane, sevoflurane, desflurane, methoxyflurane, or mixtures thereof may be used. Dosing regimens including a one-time administration, continuous and/or periodic administration are contemplated.

27 Claims, 3 Drawing Sheets

(56) References Cited

U.S. PATENT DOCUMENTS

| | | | |
|---|---|---|---|
| 6,413,987 B1* | 7/2002 | Aberg et al. | 514/319 |
| 6,669,954 B2 | 12/2003 | Crison et al. | 424/456 |
| 6,706,034 B1 | 3/2004 | Bhat | 604/890.1 |
| 6,770,636 B2 | 8/2004 | Fuchs et al. | 514/183 |
| 6,830,581 B2 | 12/2004 | Magers | 607/105 |
| 6,869,440 B2 | 3/2005 | Dobak | 607/105 |
| 2003/0152637 A1* | 8/2003 | Chasin et al. | 424/501 |
| 2003/0173287 A1 | 9/2003 | Johnston et al. | 210/496 |
| 2003/0181426 A1 | 9/2003 | Eisenach | 514/161 |
| 2003/0212123 A1 | 11/2003 | DeMello et al. | 514/411 |
| 2004/0127578 A1 | 7/2004 | Trillo et al. | 514/743 |
| 2006/0067952 A1 | 3/2006 | Chen | 424/400 |
| 2006/0198891 A1 | 9/2006 | Ravenelle et al. | 424/486 |
| 2008/0119820 A1 | 5/2008 | Phan et al. | 604/512 |
| 2008/0234389 A1 | 9/2008 | Mecozzi et al. | 514/722 |
| 2011/0159078 A1 | 6/2011 | Burton et al. | |
| 2011/0269843 A1 | 11/2011 | Phan et al. | |
| 2012/0171281 A1 | 7/2012 | Spakevicius et al. | |
| 2013/0273141 A1 | 10/2013 | Burton et al. | |

FOREIGN PATENT DOCUMENTS

| | | |
|---|---|---|
| JP | 60-501557 | 9/1985 |
| JP | 1-158353 | 6/1989 |
| JP | 5-503918 | 6/1993 |
| JP | 2006-504740 | 2/2006 |
| JP | 2010-504359 | 2/2010 |
| WO | WO 85/00011 | 1/1985 |
| WO | WO 91/03146 | 3/1991 |
| WO | WO 95/00838 | 1/1995 |
| WO | WO 96/16063 | 5/1996 |
| WO | WO 98/14174 | 4/1998 |
| WO | WO 98/17268 | 4/1998 |
| WO | WO 99/03459 | 1/1999 |
| WO | WO 99/49854 | 10/1999 |
| WO | WO 01/82952 | 11/2001 |
| WO | WO 02/085308 | 10/2002 |
| WO | WO 03/059347 | 7/2003 |
| WO | WO 03/077939 | 9/2003 |
| WO | WO 2004/014311 | 2/2004 |
| WO | WO 2004/032858 | 4/2004 |
| WO | WO 2004/087158 | 10/2004 |
| WO | WO 2004/100868 | 11/2004 |
| WO | WO 2004/103299 | 12/2004 |
| WO | WO 2005/016323 | 2/2005 |
| WO | WO 2005/016955 | 2/2005 |
| WO | WO 2005/021756 | 3/2005 |
| WO | WO 2005/023175 | 3/2005 |
| WO | WO 2005/031000 | 4/2005 |
| WO | WO 2007070694 A2 * | 6/2007 |
| WO | WO 2007/079593 | 7/2007 |
| WO | WO 2008/036858 | 3/2008 |

OTHER PUBLICATIONS

Ardente et al., "Vehicle effects on in vitro transdermal absorption of sevolurane in the bullfrog, Rana catesbeiana," *Environmental Toxicology and Pharmacology*, 25:373-379, 2008.

Fast et al., "Fluoropolymer-based emulsions for the intravenous delivery of sevoflurane," *Anesthesiology*, 109:651-6, 2008.

Office Communication issued in U.S. Appl. No. 12/863,757, dated Jun. 22, 2012.

Parlato et al., "Synthesis, characterization, and applications of hemifluorinated dibranced amphiphiles," *J. Org. Chem.*, 76:6584-6591, 2011.

Zhou et al., "The efficacy and safety of intravenous emulsified isoflurane in rats," *Anesth. Analg.*, 102:129-34, 2006.

"Anesthesia," definition located on thefreedictionary.com website located at http://www.thefreedictionary.com/anesthesia; retrieved on Oct. 23, 2010.

"Topical Amitriptyline and Ketamine Cream in Treating Peripheral Neuropathy Caused by Chemotherapy in Patients With Cancer," University of Rochester, Clinical Trial Summary located on clinicaltrials.gov website at http://Clinicaltrials.gov/show/NCT00471445, first received on May 8, 2007; last updated on Jan. 5, 2011, retrieved on Apr. 4, 2011.

Anderson et al., "Isoflurane blocks LTP of hippocampal CA1 neurons at concentrations that block recall during anesthesia," *Society of Neuroscience Abstracts*, 26(1-2):405.7, Abstract, 2000.

ASA Newsletter, "FAER announce 1997 new investigator award recipients," 61, 1997.

Bacon et al., "Regional anesthesia and chronic pain management in the 1920s and 1930s. The influence of the American Society of Regional Anesthesia," *Reg. Anesth*, 20(3):185-192, 1995. Abstract only.

Bieniarz et al., "An efficient and environmentally friendly synthesis of the inhalation anesthetic sevoflurane," *Journal of Fluorine Chemistry*, 106(1):99-102, 2000.

Breen and Park, "General anesthesia versus regional anessthesia," *Int. Anesthesiol. Clin.*, 40:61-71, 2002.

Campagna et al., "Mechanisms of actions of inhaled anesthetics," *N. Engl. J. Med.*, 348:2110-24, 2003.

Chai et al., "Epidural anaesthetic effect of the 8% emulsified isoflurane: a study in rabbits," *British Journal of Anaesthesia*, 100(1):109-115, 2007.

Chai et al., "Epidural anaesthetic effects of emulsified isoflurane (8%, v/v): A pilot study in rabbits," *Anesthesiology*, Abstract, 105:A743, 2006.

Chaplan et al., "Quantitative assessment of tactile allodynia in the rat paw," *J. Neurosci. Methods*, 53:55-63, 1994.

Delgado-Herrera et al., "Sevoflurance: approaching the ideal inhalational anesthetic, a pharmacologic, pharmacoeconomic, and clinical review," *CNS Drug Rev.*, 7:48-120, 2001.

Digger et al., "Aneaesthesia and surgical pain relief—the ideal general anaesthetic agent," *Hospital Pharmacists*, 10:432, 2003.

Dirig et al., "Effect of COX-1 and COX-2 inhibition on induction and maintenance of carrageenan-evoked thermal hyperalgesia in rats," *J. Pharmacol. Exp. Ther.*, 285:1031-8, 1998.

Eckenoff and Eckenoff, "Quantitative autoradiography of halothane binding in rat brain," The Journal of Pharmacology and Experimental Therapeutics, 285:371-376, 1998.

Eger II, "Uptake and Distribution," In: Anesthesia, Ronald D. Miller (ed.), Chapter 6, pp. 101-123, 1994.

Galinsky et al., "Basic pharmacokinetics and pharmacodynamics," In: Remington: The Science and Practice of Pharmacy (Lippincott Williams & Wilkins), Chapter 58, p. 1171, 2006.

Garcia-Fernandez et aL, "Clinical actions of subarachnoid sevoflurane administration in vivo: a study in dogs," British Journal of Anaesthesia, 95:530-534, 2005.

Gerner et al., "Topical amitriptyline in healthy volunteers," *Reg. Anesth. Pain Med.*, 28(4):289-293, 2003.

Gozzani, "New pharmacotechnique for old agents," *Revista Brasileira de Anestesiologia*, 54:623-624, 2004.

Hargreaves et al., "A new and sensitive method for measuring thermal nociception in cutaneous hyperalgesia," *Pain*, 32:77-88, 1988.

Haseneder et al., "Isoflurane reduces glutamatergic transmission in neurons in the spinal cord superficial dorsal horn: evidence for a presynaptic site of an analgesic action," *Anesth. Analg.*, 98:1718-23, 2004.

Hemmings et al., "The general anesthetic isofluran depresses synaptic vesicle exocytosis," *Mole. Phannacol.*, 67:1591-1599, 2005.

Hyderally, "Complications of spinal anesthesia," *Mt. Sinai. J. Med.*, 69:55-56, 2002.

Itah et al., "A replacement for methoxyflurane (Metofane) in open-circuit anaesthesia," *Laboratory Animals*, 38(3):280-285, 2004.

Johnson, "Potential neurotoxicity of spinal anesthesia with lidocaine," *Mayo Clinic Proceedings*, 75:921-932, 2000.

Kim and Chung, "An experimental model for peripheral neuropathy produced by segmental spinal nerve ligation in the rat," *Pain*, 50:355-363, 1992.

Koblin, "Mechanisms of Action," In: Anesthesia, Ronald D. Miller (ed.), Chapter 5, pp. 67-99, 1994.

(56) References Cited

OTHER PUBLICATIONS

Kreuer et ed., "Application of Bispectral Index® and Narcotrend® index to the measurement of the electroencephalographic effects of isoflurane with and without burst suppression," *Anesthesiology*, 101:847-54, 2004.

Liu and McDonald, "Current issues in spinal anesthesia," *Anesthesiology*, 94:888-906, 2001.

Mathias et al., "Intravenous isoflurane in lipid emulsions promotes cardiovascular and respiratory stability. Experimental model," *Rev. Bras. Anestesiol.*, 54(5):650-662, 2004.

Matute and Lopez-Garcia, "Characterization of sevoflurane effects on spinal somato-motor nociceptive and non-nociceptive transmission in neonatal rat spinal cord: an electrophysiological study in vitro," Neuropharmacology, 44:811-816, 2003.

Moller et al., "Long-term postoperative cognitive dysfunction in the elderly ISPOCD1 study. ISPOCD investigators. International Study of Post-Operative Cognitive Dysfunction," *Lancet*, 351:857-861, 1998.

Moraca et al., "The role of epidural anesthesia and analgesia in surgical practice," *Ann. of Surgery*, 238:663-673, 2003.

Murray, "The future of anesthesia delivery: from art-based science to science-based art," *ASA Newsletter*, 68, 2004.

Office Action issued in U.S. Appl. No. 11/858,497, mailed Jun. 28, 2010.

Office Action issued in U.S. Appl. No. 11/858,497, mailed Oct. 29, 2010.

Ouellette and Ouellette, "Regional Anesthesia: is it safer?," *CRNA*, 6:70-78, 1995.

PCT International Preliminary Report on Patentability issued in International Application No. PCT/US2009/031706, mailed Aug. 5, 2010.

PCT International Search Report and Written Opinion issued in International Application No. PCT/US2009/031706, mailed Apr. 17, 2009.

PCT International Search Report and Written Opinion, issued in International Application No. PCT/US2007/079097, dated May 7, 2008.

Petersen-Felix et al., "Analgesic effect in humans of subanaesthetic isoflurane concentrations evaluated by experimentally induced pain," *British Journal of Anaesthesia*, 75:55-60, 1995.

Rampil and King, "Volatile anesthetics depress spinal motor neurons," *Anesthesiology*, 85:129-134, 1996.

Rasmussen et al., "Does anaesthesia cause postoperative cognitive dysfunction? A randomised study of regional versus general anaesthesia in 438 elderly patients," *Acta Anaesthesiologica Scandinavica*, 47:260-266, 2003.

Remington: The Science and Practice of Pharmacy, $20^{th}$ Ed., Baltimore, MD: Lippincott Williams & Wilkins, pp. xiv-xv (Table of Contents), 2000.

Robinson and Zhuo, "Pharmacological interventions at the spinal cord," *Methods in Molecular Medicine*, 84:217-222, 2003.

Rogers et al., "Knowledge and communication difficulties for patients with chronic heart failure: qualitative study," *BMJ*, 321:605-607, 2000.

Sevorane™, Information for Health Professionals Presentation, website located at www.medsafe.govt.nz/profs, retrieved on Apr. 27, 2005.

Sorkin et al., "Pain models display differential sensitivity to Ca2+-permeable non-NMDA glutamate receptor antagonists," *Anesthesiology*, 95:965-973, 2001.

Sumikura and Arendt-Nielsen, "MAC reduction after intrathecal coadministration of GABA (A) agonist and glutamate antagonist in rats," *J. Anesth.*, 17:92-97, 2003.

Takenoshita et al., "Halothane suppresses inhibitory monosynaptic transmission," Progress in Anesthetic Mechanism, 3:326-329, 1995.

Ting, "Low flow anesthesia: advantages and disadvantages, Part 1," *Clinical Window*, 1-4, 2003.

Tung, "New anesthesia techniques," *Thorac. Surg. Clin.*, 15:27-38, 2005.

Yaksh and Rudy, "Chronic catheterization of the spinal subarachnoid space," *Physiol. Behav.*, 17:1031-6, 1976.

Yaksh et al., "An automated flinch detecting system for use in the formalin nociceptive bioassay," *J. Appl. Physiol.*, 90:2386-2402, 2001.

Yamauchi et al., "Inhibitory action of sensory transmission by inhalational anesthetics in the spinal cord," (English Abstract), *Masui.*, 52:240-50, 2003.

Yang et al., "Research on preferential delivery of emulsified isoflurane to the in situ spinal cord of the goat," *Anesthesiology*, Abstract, 105:A409, 2006.

Zhang et al., "Both cerebral GABA (A) receptors and spinal GABA (A) receptors modulate the capacity of isoflurane to produce immobility," *Anesth. Analg.*, 92:1585-9, 2001.

Zhang et al., "Glycine receptors mediate part of the immobility produced by inhaled anesthetics," *Anesth. Analg.*, 96:97-101, 2003.

Office Action issued in Japanese Application No. 2010-544418, mailed Oct. 15, 2014, and English language translation thereof.

Haynes et al., "Long duration local anesthesia with lecithin-coated microdroplets of methoxyflurane: studies with human skin," *Regional Anesthesia*, 16:173-180, 1991.

Office Action issued in Japanese Application No. 2015-151459, mailed Apr. 25, 2016, and English language translation thereof.

Office Action issued in European Application No. 09703373.2, mailed Jul. 4, 2016.

Smith and Stump, "Isoflurane anesthesia in the African clawed frog (*Xenopus laevis*)," *Contemp Top Lab Anim Sci.*, 39(6):39-42, 2000. (Abstract only).

\* cited by examiner

VOLATILE ANESTHETIC COMPOSITIONS COMPRISING EXTRACTIVE SOLVENTS FOR REGIONAL ANESTHESIA AND/OR PAIN RELIEF

The present application is a national phase application under 35 U.S.C. §371 of International Application No. PCT/US2009/031706 filed Jan. 22, 2009 which claims benefit of priority to U.S. Provisional Application Ser. No. 61/022,665 filed Jan. 22, 2008, the entire contents of which is hereby incorporated by reference.

BACKGROUND OF THE INVENTION

1. Field of the Invention

The present invention relates generally to the fields of anesthesia and pain management. More specifically, the present invention provides methods for reducing pain by regionally delivering a solution comprising a volatile anesthetic and an extractive solvent to a subject in need of pain reduction or anesthesia.

2. Description of Related Art

Millions of people suffer from pain. The pain may be minor, such as headaches, acute lower back pain, and acute muscle pain, or severe, such as chronic pain. Chronic pain may be associated with cancer treatment, HIV, diabetes, or other conditions. Chronic pain can be difficult to treat, with many chronic pain sufferers noting that their pain is not well controlled with current pain medications or that their medications have significant associated adverse effects (e.g., nausea and vomiting, dependence, tolerance, etc.).

In an attempt to address the problem of chronic pain management, intrathecal infusion pumps and neurostimulators have been developed. Intrathecal infusion pumps are aimed at continuous, or near continuous delivery of liquid anesthetic and/or analgesic agents. Many of these infusion pumps are totally implantable, which helps to reduce the risk of infection when compared to the long-term use of external systems. The infusion pump may also be programmable to allow patients or their clinicians to adjust dosing amounts or daily delivery schedule, helping to meet a patient's changing needs.

Neurostimulators are available in various forms and stimulate nerves to relieve pain. Both intrathecal pumps and neurostimulators have drawbacks, including the onset of tolerance, with the treatments becoming less effective over time. In addition, neither intrathecal infusion pumps nor neurostimulators are suitable for anesthetizing a patient prior to a surgery.

Various approaches for inducing anesthesia or analgesia are known. Systemic delivery of a general anesthetic renders a patient unconscious and unaware of the surgery. In contrast, anesthetics may be applied regionally, for example, to the spine, epidurally, or near a nerve in a nerve block to anesthetize only a portion of the patient's body. For general anesthesia, delivery of a general anesthetic to a patient prior to surgery is typically performed using an initial i.v. injection of an anesthetic followed by intubation and administration of an inhalable anesthetic gas. It is worthwhile to note that the mechanism of action for general anesthesia is still not completely understood.

Considerable negative side effects may result from administration of general anesthesia. A large tube has to be placed into the trachea, which can result in trauma to the upper airway. Many patients report postoperative hoarseness and tenderness of the mouth and throat. In addition, the large amount of gases required to flood the body to reach the targeted organs can have an adverse affect on the non-targeted organs, especially the heart, with an increased risk of cardiopulmonary morbidity during general anesthesia. Especially in the elderly, there is substantial evidence for prolonged cognitive dysfunction following general anesthesia (Moller et al., 1998). Additionally, regional anesthetic techniques appear to lead to less overall morbidity and mortality from cardiopulmonary causes as compared to general anesthesia (Rasmussen et al., 2003; Rogers et al., 2000)

Certain risks are also associated with inhalation administration of a volatile anesthetic, e.g., during general anesthesia. Volatile anesthetic compositions formulated for inhalation generally have relatively low boiling points and high vapor pressures. Volatile anesthetic compositions are often flammable or explosive in both their liquid and vapor states. Further, inhalation of vapors by health care personnel can cause drowsiness, which is not desirable in an operating room environment. Thus, substantial care must be taken to safely handle volatile anesthetics in order to minimize both the risk of inhalation by medical personnel and the risk of fire or explosion, and care must be taken to try to ensure that there is little or no release of the volatile anesthetic into the atmosphere at all stages of handling.

Clearly, there exists a need for improved methods for pain management and regional anesthesia. Further, there exists a need for volatile anesthetic compositions that have reduced risks, as described above, associated with their use. There is also a need for methods for delivering such improved volatile anesthetic compositions, e.g., for treating pain or for use in a surgical procedure.

SUMMARY OF THE INVENTION

The present invention overcomes limitations in the prior art by providing improved volatile anesthetic compositions and methods for administering anesthetics and reducing pain in a subject, such as a human or animal patient or laboratory animal such as a mouse or rat, in need of such pain reduction. In certain embodiments, the present invention provides an anesthetic composition comprising a volatile anesthetic dissolved in a aqueous-based solution, wherein the solution further comprises a pharmaceutically acceptable extractive solvent (e.g., DMSO, etc.).

The presence of an extractive solvent in the solution comprising the volatile anesthetic may provide substantial advantages, including improving the physical characteristics, pharmacological properties, and/or the ease of use of the anesthetic solution. The extractive solvent may interact with the volatile anesthetic (e.g., isoflurane) in a non-azeotropic fashion to effectively reduce vaporization or evaporation of the volatile anesthetic. In this way, the shelf-life, durability, and/or ease of use of a volatile anesthetic in solution may be improved. The presence of an extractive solvent in the anesthetic solution may also improve the ease of mixing the solution prior to administration; in certain embodiments, a sonicator is not required to mix the anesthetic solution prior to use. Additionally, the pharmacokinetics of the volatile anesthetic may be altered by the presence of an extractive solvent to provide improved pain relief. For example, without wishing to be bound by any theory, the inventors anticipate that the extractive solvent may function in certain embodiments as a reservoir for the volatile anesthetic to maintain the volatile anesthetic in a particular region more effectively and/or help deliver the volatile anesthetic to site(s) of action. Reduced volatility of the volatile anesthetic in solution may also improve the ease of handling the anesthetic compositions. Further, the reduced vaporization of a volatile anesthetic in solution due to the presence of an extractive solvent may also reduce concerns, as described above, regarding a possible risk of fire and/or inhalation by medical personnel.

It is understood that the invention does not include administration of a volatile anesthetic to a subject by inhalation of the volatile anesthetic vapor alone. The methods preferably comprise the local or regional delivery, such as, for example, transdermal, topical, mucosal, buccal, rectal, vaginal, intramuscular, subcutaneous, intrathecal or epidural delivery, of a volatile anesthetic in an aqueous based solution to the subject in an amount effective to reduce chronic or acute pain. In other embodiments, an anesthetic composition of the present invention may be administered topically in an amount sufficient to reduce pain. More specifically, the inventors have discovered that, in certain embodiments, anesthetic compositions of the present invention may be administered topically to a human subject to achieve local pain reduction. In certain embodiments, and the anesthetic may be delivered to the subject to anesthetize the subject prior to a surgery. It should be understood, that as used herein, the phrase "pain reduction" is intended to cover pain reduction as a result of anesthesia, analgesia, and/or the inhibition of neural impulses involved in pain perception, e.g., via partial nerve conduction block. In certain embodiments, the compositions of the invention may be delivered to a portion of the subject in an amount and in a manner effective to reduce pain. In other embodiments, the compositions of the invention may be delivered to a portion of the subject in an amount and in a manner effective to reduce pain without substantially interfering with motor function of the subject.

The present invention has several substantial advantages over previously used methods for regional anesthesia. These advantages include: (1) the volatile anesthetics of the present invention are rapidly titratable, thus administration of a volatile anesthetic according to the present invention can result in a very quick onset of analgesia or regional anesthesia. (2) The present invention allows for the quick dissipation of anesthetics after administration; thus the anesthesia or analgesia may be rapidly ended. These properties are of particular value to a practitioner, as it may be desirable for a practitioner to quickly alter the dosing of a regional anesthesia or analgesia as desired. (3) Certain drugs presently used for regional anesthesia may not be effectively used on various individuals for a variety of reasons, including tolerance, drug interactions, paradoxical responses, etc. Additionally, (4) the volatile anesthetics of the present invention are generally non-opioid compounds, which provides various benefits for a practitioner, as opioids possess certain disadvantages, including tolerance, drug interactions, and dependence etc.

An aspect of the present invention relates to a method for reducing pain in a subject in need of such pain reduction comprising regionally or locally delivering to the subject a volatile anesthetic dissolved in a solution comprising an extractive solvent in an amount effective to reduce pain. If the administration is intrathecal or epidural, then the solution may be free or essentially free of a lipid emulsion. In preferred embodiments, the anesthetic is delivered by routes other than intravenously in that intravenous delivery could potentially give rise to general anesthesia that, while not specifically excluded from the present invention, is not a preferred aspect. Preferred volatile anesthetics are the halogenated ether anesthetic dissolved in an aqueous, pharmaceutically acceptable solution. The anesthetic may preferably be delivered intrathecally, epidurally, or in a nerve block procedure, to relieve, for example, chronic pain or acute pain. In certain embodiments, the anesthetic may be administered locally or topically prior to a procedure such as a venipuncture, an injection (e.g., Botox™), a peripheral venous cannulation, incision or other procedure; in other embodiments, the anesthetic may be administered via non-topical routes. The anesthetic may be topically applied prior to a cosmetic procedure such as hair removal, tattoo application or removal, and/or a mammography.

Various extractive solvents may be used with the present invention. For example, dimethyl sulfoxide (DMSO), N-Methyl-2-pyrrolidone (NMP), dimethylisosorbide, ethanol, propanol, or isopropanol may be the extractive solvent. The extractive solvent may comprise from about 10% to about 75% of the solution, 25% to about 75% of the solution, 10% to about 50% of the solution, from about 10% to about 25% of the solution, or from about 25% to about 50% of the solution.

In certain embodiments, a volatile anesthetic in solution is delivered to anesthetize a portion of the subject prior to a surgery. The volatile anesthetic may be a halogenated volatile anesthetic selected from the group consisting of isoflurane, halothane, enflurane, sevoflurane, desflurane, methoxyflurane, and mixtures thereof. In certain embodiments, isoflurane is used. The solution, such as an isoflurane solution, may be prepared in a concentration of about 5 ng/ml solution to about 100 ng/ml solution. The solution may comprise from about 0.1% to about 15% v/v, 1% to about 75% v/v, 1% to about 50% v/v, 5% to about 50% v/v, 5% to about 75% v/v, from about 10% to about 50% v/v, or about 10% v/v anesthetic in solution. The anesthetic may be isoflurane and/or the solution may be artificial cerebrospinal fluid. When administered epidurally or intrathecally it is desirable to achieve a concentration of from about 250 ng/ml to about 50,000 ng/ml of active agent in the spinal fluid. The delivery of the active agent may be continuous, periodic, a one-time event, or the active agent may be both periodically administered and continuously administered to the subject on separate occasions. The reduction may comprise elimination of pain perception of a portion of the body of the subject.

In certain embodiments, the compositions of the invention may be delivered to a portion of the subject in an amount and in a manner effective to reduce pain without substantially interfering with motor function of the subject, for example, by varying the dosage, amount, concentration, frequency of administration, and/or timing of administration. Tests useful for the evaluation of motor function include, for example, but are not limited to, the Minnesota Rate of Manipulation (MRM) test (Fleishman, 1964, Abilities and motor skill. In: The structure and measurement of physical fitness Prentice-Hall, Inc.: Englewood Cliffs, N.J., 1964, pp. 23-24), the Upper Extremity Function Test (UEFT) (Carroll, 1965, J Chron Dis 18: 479-491), the Purdue Pegboard test (Tiffin et al., 1948, J Appl Psychol 32: 234-247), the Jebsen test of hand function (Jebsen et al., 1969, Arch Phys Med Rehab 50: 311-319), the Nine-Hole Peg test (Kellor et al., 1971, Am J Occup Ther 25: 77-83), the Smith hand function evaluation (Smith, 1973, Am J Occup Ther 27: 244-251), the Box and Block Test (BBT) (Holser et al., 1960, Box and Block test. In: Cromwell F S (ed) Occupational therapists manual for basic skills assessment: primary prevocational evaluation Fair Oaks Printing Company Pasadena, Calif., pp. 29-31), the Physical Capacities Evaluation of Hand Skill (PCE) (Bell et al., 1976, Am J Occup Ther 30: 80-86), the Action Research Arm (ARA) test (Lyle, 1981, Int J Rehabil Res 4: 483-492), the Sollerman hand function test (Sollerman et al., 1995, Scand J Plast Reconstr Surg Hand Surg 29: 167-176), Lower Extremity MOtor COordination Test (LEMOCOT) (Desrosiers et al., 2005, Arch Phys Med Rehabil 86, 993-98), the Fugl-Meyer Assessment (Fugl-Meyer et al., 1975, Scand J Rehabil Med 7:13-31), Berg Balance Scale (Berg et al., 1995, Scand J Rehabil Med 27:27-36; Berg et al., 1989, Physiother Can 41:304-11, Berg et al, 1992, Arch Phys Med Rehabil 73:1073-80; Stevenson et al., 1996, Arch Phys Med Rehabil 1996; 77:656-62), 5-meter walking test (5MWT) (Salbach et al., 2001, Arch Phys Med Rehabil 82:1204-12), 2-minute walking test (Wade, 1992, Measurement in neurological rehabilitation. New York: Oxford Univ Pr; Guyatt et al., 1984, Thorax 39:818-22), and the Functional Autonomy Measurement System (Hébert, 1988, Age Ageing 17:293-302), all of which references are incorporated herein in their entirety.

Preferably, in that the solution is intended for parenteral or topical administration, the aqueous solution comprising the volatile anesthetic is sterile. This can be achieved by ensuring that all starting materials are sterile and maintaining them under sterile conditions prior to administration. As for the underlying aqueous solution, the nature of the solution is not believed to be critical, and solutions such as normal saline or even solutions formulated to mimic natural body fluids, such as artificial cerebrospinal fluids, are contemplated.

Yet another aspect of the present invention involves a sealed container comprising an anesthetic solution of the present invention. The interior of the container may be sterile. The container may comprise a rubber stopper which can be easily pierced by an injection needle. The container may comprise the chamber portion of a syringe. The container may comprise a drip chamber. The drip chamber may be coupled to a catheter. The catheter may be an epidural catheter or an intrathecal catheter. The container may be a plastic bag, a glass bottle, or a plastic bottle. The container may be coupled to an infusion pump. The infusion pump may be an intrathecal pump, an epidural delivery infusion pump, or a patient control analgesia (PCA) pump. The infusion pump may be programmable.

The terms "inhibiting," "reducing," or "preventing," or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method or composition of the invention, and vice versa. Furthermore, compositions of the invention can be used to achieve methods of the invention.

Throughout this application, the term "about" is used to indicate that a value includes the inherent variation of error for the device, the method being employed to determine the value, or the variation that exists among the study subjects.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual and partial numbers within that range, for example, 1, 2, 3, 4, 5, 5.5 and 6. This applies regardless of the breadth of the range.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DETAILED DESCRIPTION

Figure 1:
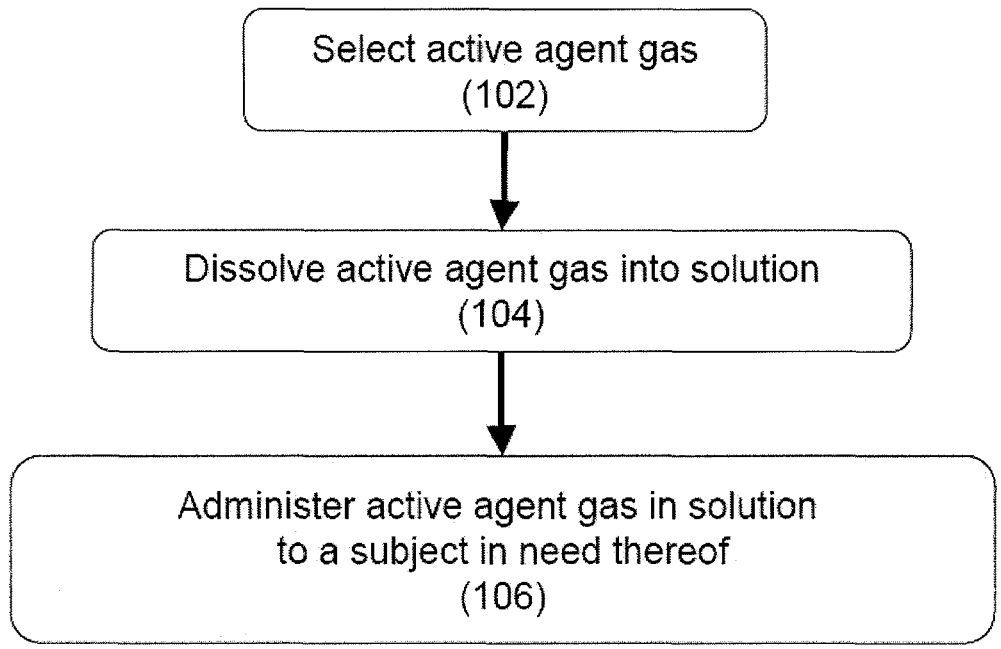
FIG. 1: A flowchart representing a general method for delivering an anesthetic gas to a subject.

The present invention overcomes limitations in the prior art by providing improved volatile anesthetic compositions comprising a volatile anesthetic dissolved in a aqueous-based solution, wherein the solution further comprises a pharmaceutically acceptable extractive solvent. The presence of the extractive solvent may provide certain advantages for the anesthetic composition, including a reduction in the anesthetic vapors emitted from the solution (e.g., reducing risks associated with the flammability of the vapors and/or inhalation by medical personnel), improvements in the shelf-life or durability of the composition, and/or improved pharmacokinetics of the anesthetic composition. For example, the extractive solvent may interact with the volatile anesthetic (e.g., isoflurane) in a non-azeotropic fashion to effectively reduce vaporization or evaporation of the volatile anesthetic. In this way, the shelf-life and/or durability of a volatile anesthetic in solution may be improved. Additionally, the pharmacokinetics of the volatile anesthetic may be altered to provide improved pain relief. For example, without wishing to be bound by any theory, the inventors anticipate that the extractive solvent may function in certain embodiments as a reservoir for the volatile anesthetic to maintain the volatile anesthetic in a particular region more effectively and/or help deliver the volatile anesthetic to site(s) of action. In various embodiments, the presence of an extractive solvent in the anesthetic solution can also allow for mixing the solution prior to administration without the use of a sonicator.

The present invention also provides methods for using such anesthetic compositions for reducing pain in a subject in need of such pain reduction. Specifically, although volatile anesthetics are normally inhaled during a general anesthesia procedure, the inventors have discovered that volatile anesthetics may be dissolved in a solution and delivered regionally or locally (e.g., transdermally, topically, mucosally, buccally, rectally, vaginally, intramuscularly, subcutaneously, intrathecally, epidurally, or in a nerve block) to inhibit or block pain perception. In certain embodiments, the anesthetic may be administered locally or topically prior to a procedure such as a venipuncture, an injection (e.g., Botox™), a peripheral venous cannulation, incision, or other procedure; in these embodiments, the administration of the anesthetic preferably reduces or prevents pain from being felt by the subject prior to and during a medical procedure, including minor surgical procedures, non-surgical procedures, and cosmetic procedures including, e.g., hair removal, tattoo application, tattoo removal, and mammography.

In general, the methods may involve the delivery of a halogenated ether anesthetic to the subject in an amount effective to reduce pain. The present invention may be used for pain management of chronic or acute pain. In other embodiments, the anesthetic may be delivered to a subject to anesthetize at least a portion of the subject prior to a surgery. In certain embodiments, the present invention may be used to reduce or eliminate pain in a subject without also causing a loss of consciousness of the subject. In other embodiments, the present invention may be used to reduce or eliminate pain in a subject without also substantially interfering with motor function of the subject.

Extractive Solvents

Anesthetic compositions of the present invention may contain a solvent, such as an extractive solvent, in combination with a volatile anesthetic. The phrase "extractive solvent," as used herein, refers to a solvent which may interact with a volatile anesthetic in solution to reduce the volatility of the volatile anesthetic without chemically reacting to the anesthetic. Certain extractive solvents interact in a non-azeotropic fashion with a volatile anesthetic; nonetheless, the term "extractive solvent," as used herein, may include certain compounds which interact with a volatile anesthetic to form an azeotropic or pseudoazeotropic solution as long as the vapor pressure or evaporation of the volatile anesthetic from the solution is reduced. As described below, various extractive solvents are envisioned for use with the present invention, e.g., DMSO, NMP, etc. The extractive solvents used with the present invention are preferably pharmacologically acceptable. The exact concentration of an extractive solvent may be determined empirically and may vary according to the specific volatile anesthetic used. Particular care should also be taken to choose a concentration of an extractive solvent which results in little or no toxicity when administered. It will be understood that, although certain extractive solvents may exhibit properties which might be used in various separation procedures (e.g., extractive distillation), extractive solvents according to embodiments of the present invention are preferably included in pharmacological mixtures or solutions comprising a volatile anesthetic in order to reduce the volatility of, rather than "extract," the volatile anesthetic.

Including an extractive solvent in an anesthetic composition may increase the ease with which one can admix the solution prior to administration. For example, in certain embodiments, sonication of the anesthetic solution prior to administration is not required when an extractive solvent is included in the anesthetic solution. This advantage may be particularly useful in instances (e.g., chronic administration) where the presence of a sonicator could be noisy or distracting, such as an operating room, and the elimination in the noise of a sonicator may also create an improved environment for a conscious patient receiving an anesthetic solution, e.g., chronically or intermittently for pain relief. Eliminating the need for a sonicator, or other similar device, may also be particularly useful for reducing costs associated with administration of an anesthetic composition according to the present invention. The reduction in the bulk associated with the presence of a sonicator can beneficially improve patient mobility. For example, in instances where a patient may receive repeated administrations of an anesthetic composition via a pump for analgesia, the reduced amount of equipment can improve mobility since the patient is not required to additionally move a sonicator.

Extractive solvents are known in the art and are typically used in extractive distillation for separating compounds with similar boiling points by retarding the vapor pressure of the principal component, thereby making possible an efficient separation which would not at all occur in the absence of such solvent. For example, U.S. Pat. No. 5,230,778 describes the purification of isoflurane by extractive distillation using extractive solvents such as dimethylformamide. U.S. Pat. No. 5,336,429 describes solvents for cleaning electronic components and for degreasing metals comprising isoflurane and a lower alcohol or an ester, although these compositions are described as azeotropic mixtures with virtually constant boiling points. In contrast, the present invention provides pharmaceutical preparations, e.g., for inducing analgesia and/or regional anesthesia. Certain extractive solvents known in the art, such as acetone as described in U.S. Pat. No. 5,230,778, may be sufficiently toxic to limit their inclusion in pharmaceutical preparations at higher concentrations.

In certain embodiments, an extractive solvent may interact as an azeotropic mixture with an anesthetic and reduce the volatility of the anesthetic. For example, ethanol may interact in an azeotropic fashion with a volatile anesthetic as described in U.S. Pat. No. 5,230,778.

Various concentrations of an extractive solvent may be used with the present invention. For example, a solution of the present invention comprising a volatile anesthetic may comprise about 1%-99%, 1%-60%, 5%-50%, 10%-40%, 5%-25%, 10%-30%, 10%-25%, 25%-50%, 10%-75%, 25%-75%, 10%-65%, 25%-65%, 10%-60%, 25%-60%, 5%, 10%, 20%, 25%, 30%, 35%, 40%, 45%, 50%, 55%, 60%, 65%, 70%, 75%, 80% or any range derivable therein, of an extractive solvent.

In certain embodiments, the extractive solvent is dimethylsulfoxide (DMSO) or N-Methyl-2-pyrrolidone (NMP). In other embodiments, an extractive solvent such as dimethylformamide, dimethylacetamide, or dimethylisosorbide may be used. In instances where acetone is used, care should be taken to choose an appropriate dose in order to minimize any possible toxicity.

In various embodiments, it is envisioned that a medically acceptable alcohol, such as ethanol, propanol, or isopropanol may be used. In these embodiments, the concentration of the alcohol used is sufficiently dilute in solution such that little or no neuron death occurs as a result of injection of the solution near a nerve.

A single extractive solvent or multiple extractive solvents may be present in an anesthetic composition of the present invention. For example, in certain embodiments, only a single extractive solvent (e.g., DMS or NMP) is present in a solution comprising a volatile anesthetic. In other embodiments, 2, 3, 4, or more extractive solvents may be present in a solution comprising a volatile anesthetic. In certain embodiments, only a single volatile anesthetic (e.g., isoflurane) is present in an anesthetic solution of the present invention; in other embodiments, 2, 3, 4 or more volatile anesthetics may be present in an anesthetic composition of the present invention.

N-Methyl Pyrrolidone

N-Methyl-2-pyrrolidone (NMP) is an extractive solvent which may be included in anesthetic compositions according to the present invention. NMP is a chemical compound with 5-membered lactam structure. It is a clear to slightly yellow liquid miscible with water and solvents including ethyl acetate, chloroform, benzene and lower alcohols or ketones. NMP is also referred to by the chemical names 1-methyl-2-pyrrolidone or N-methyl-2-pyrrolidinone and m-pyrrole. NMP belongs to the class of dipolar aprotic solvents which also includes dimethylformamide, dimethylacetamide and dimethyl sulfoxide. Due to its good solvency properties, NMP has been used to dissolve a wide range of chemicals, particularly in the polymers field. It also used as a solvent for surface treatment of textiles, resins and metal coated plastics or as a paint stripper.

NMP has been used in the medical industry to improve the solubility of poorly soluble drugs in certain pharmaceutical formulations. For example, NMP has been used with various drugs in veterinary medicine. Several patents have been issued, claiming improvements in drug solubility by the use of NMP, as well as its applicability in topical and transdermal pharmaceutical products for humans.

The relatively non-toxic properties of NMP make it particularly suitable for use as an extractive solvent with the present invention. NMP has a favorable toxicity profile making it a suitable candidate for use in a variety of topical, transdermal and parenteral dosage forms. NMP is available in GMP grade under the trademark Pharmasolve N-Methyl-2-pyrrolidone sold by International Specialty Products (ISP; New Jersey, USA).

DMSO

Dimethyl sulfoxide (DMSO) is used in certain embodiments of the present invention as an extractive solvent. DMSO has the formula $(CH_3)_2SO$. DMSO is a polar aprotic solvent that dissolves both polar and nonpolar compounds and is miscible in a wide range of organic solvents as well as water.

DMSO is a relatively non-toxic compound, which makes it particularly suitable for use as an extractive solvent with the present invention. The relative lack of toxicity of DMSO is well established, and the potential use of DMSO for medical purposes was established Stanley Jacob at the University of Oregon Medical School team, who discovered DMSO could penetrate the skin and other membranes without damaging them and could carry other compounds into a biological system. DMSO has also been used as a cryoprotectant and as an anti-inflammatory agent. Dimethyl sulfoxide dissolves a variety of organic substances, including carbohydrates, polymers, peptides, as well as many inorganic salts and gases.

In various embodiments, it is envisioned that lower concentrations, e.g., as low as from about 5% to about 10%, of DMSO in a solution comprising a volatile anesthetic may be sufficient to eliminate the need for sonication of the solution prior to administration. Higher concentrations, e.g., from about 25% to about 75% or higher, from about 30% to about 60% or higher, of DMSO in a solution comprising a volatile anesthetic may be sufficient to alter the pharmacokinetics of the volatile anesthetic in such a way to allow for an increased duration of analgesic or anesthetic effects.

Anesthetic Agents

In general, the halogenated ether anesthetics or volatile anesthetics suitable for use with the described methods include agents which, although often liquid at room temperature, are capable of easily being becoming gaseous or are already gaseous at room temperature and can reduce pain without significant side effects. It may be desirable, for example, to select an anesthetic that is minimally metabolized by the body or is otherwise inert. In this way, liver and kidney toxicity may be minimized. Similarly, it may be desirable for the anesthetic to have a short half-life, or be fast acting to promote titratability (i.e., the subject can easily adjust the delivery amount for the amount of pain he or she is experiencing). An active agent gas that does not produce tolerance (unlike opioids or local anesthetic agents) or dependence (like opioids) may also be desirable. The methods of the present invention may also be used to deliver another volatile agent to a subject, e.g., topically, locally, or in a regional anesthesia procedure. The volatile agent may be an anesthetic or small molecule.

Volatile anesthetics are a well known class of anesthetics which includes halogenated ether compounds, isoflurane, sevoflurane, halothane, enflurane, desflurane, methoxyflurane, and diethyl ethers. In certain embodiments xenon may also be used with the present invention. A single anesthetic or mixtures of the above anesthetics may be particularly suitable for use with the methods described herein.

In various embodiments, a gas anesthetic may used with the present invention. For example, the gas anesthetic may be dissolved in a solution according to the present invention and administered in a regional or local anesthesia procedure, such as such as transdermally, topically, mucosally, buccally, rectally, vaginally, intramuscularly, subcutaneously, epidurally, intrathecally, or in a nerve block procedure. Gas anesthetics other than halogenated anesthetics are contemplated, and examples or which include xenon, nitrous oxide, cyclopropane, and ether. In various embodiments, other biologically active gases (e.g., nitric oxide, etc.) may be delivered in a solution to a subject according to the present invention.

More than one anesthetic may be administered at one time, and different anesthetics may be administered at various times throughout a single treatment cycle. For example, 2, 3, 4 or more anesthetic agents may be simultaneously or repeatedly administered to a subject. When compounds are repeatedly administered to a subject, the duration between administration of compounds may be about 1-60 seconds, 1-60 minutes, 1-24 hours, 1-7 days, 1-6 weeks or more, or any range derivable therein. In some instances, it may be desirable to stage the delivery of different halogenated ether compounds depending on their physical and physiological properties.

Dosing

The amount of the anesthetic to be administered, e.g., intrathecally or epidurally, depends on the particular indication desired. For example, the dose will depend on the type of pain intended to be treated. The dose may be different, for instance, if the delivery of the anesthetic is intended to reduce chronic pain as opposed to acute pain. Similarly, the dose may be different if the active agent will be used to anesthetize a subject (locally or generally). The subject's physical characteristics may also be important in determining the appropriate dosage. Characteristics such as weight, age, and the like may be important factors. For example, the anesthetic may have increased potency with age, as has been demonstrated in the case of the volatile anesthetic isoflurane.

The temperature of the volatile anesthetic may also be considered as a factor in selecting an appropriate dose, as the solubility of many anesthetics may be affected by the temperature of the anesthetic and/or aqueous solution. For example, increases in temperature may increase the solubility, and thus potency, of the active agent; this property has been demonstrated with certain anesthetic agents. The particular dosage may also be dependent on the dosing regime chosen. For example, the active agent may be delivered continuously or periodically. Conversely, the active agent may be administered as a single administration as a one-time event.

Volatile anesthetics (e.g., halogenated anesthetic compounds) may be infused in amounts leading to spinal fluid levels in the range of about 250 to about 50,000 nanograms/ml, depending on the anesthetic selected and the desired effect. In certain embodiments, a halogenated anesthetic or volatile anesthetic may be administered to achieve cerebrospinal fluid (CSF) concentration of from about 5 to about 500,000 nanograms/ml. While the dose range will vary depending on the compound selected and patient variability, it is generally true that lower doses such as from about 0.01 to about 10,000 nanogram/ml are more suitable for treating minor to moderate pain, while higher doses such as from about 10000 nanogram/ml to about 500,000 nanogram/ml or more are suitable for treating severe pain and inducing anesthesia. Of course, the doses may be given once (e.g., for a minor single occurrence of pain), repeatedly (e.g., for moderate or chronic pain), or continuously (e.g., for severe pain or anesthesia purposes). Combinations of these dosing regimes may also be used. For example, a subject suffering from severe pain may require continuous dosing with periodic additional dosing needed for breakthrough pain.

In embodiments where an anesthetic (e.g., a volatile anesthetic, isoflurane, etc.) is admixed with a solution, such as saline or an artificial CSF solution, the concentration of the volatile anesthetic may vary. For example, a solution may contain an anesthetic in a v/v ratio of from about 1 to about 99%, from about 10 to about 75%, from about 10 to about 50%, from about 20 to about 50%, from about 1 to about 50%, from about 1 to about 45%, from about 1 to about 40%, from about 1 to about 35%, from about 1 to about 30%, from about 1 to about 25%, from about 1 to about 20%, from about 1 to about 15%, from about 1 to about 10%, from about 1 to about 5%, from about 0.5 to about 5%, from about 0.1 to about 5%, from about 0.1 to about 2.5%, from about 0.5 to about 2.5%, or any range derivable therein. In these embodiments, the anesthetic may be a volatile anesthetic, such as isoflurane, and the solution may be an artificial cerebrospinal fluid (ACSF) solution.

The dosing and manner of delivery of the compositions of the invention may be adjusted to achieve pain reduction without substantially interfering with motor function of the subject, for example, by varying the amount, concentration, frequency of administration, and timing of administration.

The anesthetic solution may also contain one or more additive, such as a surfactant, PVP, a polymers, a antimicrobial agent, etc. In certain embodiments, an anesthetic composition of the present invention may comprise about: 0.1-50% of a volatile anesthetic such as isoflurane, methoxyflurane, or sevofluorane, 1-99% of an extractive solvent such as NMP or DMSO, 0-90% saline, and 0-10% other additive(s) (e.g., a surfactant, PVP, etc.). In some embodiments, it may be desirable to produce a concentrated formulation which may be subject to a final dilution prior to administration.

In various embodiments and as shown in the below examples, a solution of about 10% volatile anesthetic, such as isoflurane, may be used; this solution may be administered as a bolus injection, continuously, and/or repeatedly to achieve analgesia and/or anesthesia. Thus, as demonstrated in the below examples, a 10% v/v solution of a volatile anesthetic may be used to induce analgesia. Higher concentrations of volatile anesthetic may be used, in various embodiments, to induce a regional anesthesia.

Method of Active Agent Delivery

Anesthetics of the present invention may be delivered regionally or locally. "Regional" or "local" anesthesia, as used herein, is distinct from general anesthesia and refers to anesthetic procedures which allow for the preferential delivery of an anesthetic to a specific region of the body, such as near a nerve or a nerve bundle. In contrast, general anesthesia allows for the systemic administration of an anesthetic, e.g., via intravenous administration. Regional or local anesthesia typically allows for a lower total body concentration (although elevated local concentrations) of an anesthetic to be administered to a subject for analgesia or diminished pain perception of at least a portion of the subject's body. For example, intrathecal anesthesia, epidural anesthesia, and nerve blocks are examples of regional or local anesthesia. Specific concentrations of anesthetics which may be used for regional or local anesthesia include from about 250 to about 50,000 nanogram/ml, from about 250 to about 25000 nanogram/ml, from about 250 to about 10000 nanogram/ml, from about 250 to about 5000 nanogram/ml, from about 250 to about 2500 nanogram/ml, or from about 250 to about 1000 nanogram/ml. The specific concentration of anesthetic used may vary depending on the desired effect, and in various embodiments the anesthetic composition is titrated for effect; thus the concentration of anesthetic used or achieved in tissues may vary depending on the specific desired result (e.g., regional anesthesia as compared to analgesia) and/or the particular characteristics of the patient, such as sensitivity to the anesthetic.

The present invention may be used with various nerve block procedures. Nerve block procedures according to the present invention may be performed with or without ultrasound visualization; for example, an ultrasound machine may be used to visualize the region of the body involved a the nerve block procedure, such as, e.g., various nerve bundles in the shoulder, neck, lower back, etc. The inventors envision that the present invention may be used in conjunction with a variety of surgical procedures, including, for example, but not limited to, knee replacement, a hip replacement, shoulder replacement, and/or birthing-related procedures.

In certain embodiments, compositions and methods of the present invention may be used for pain management. Pain management is distinct from general anesthesia in that a lower total body concentration of an anesthetic may be administered to a subject to in order to increase analgesia or decrease perception of pain, preferably without rendering the subject unconscious. Specific concentrations of anesthetics which may be used for pain management include from about 250 to about 50,000 nanogram/ml, from about 250 to about 25000 nanogram/ml, from about 250 to about 10000 nanogram/ml, from about 250 to about 5000 nanogram/ml, from about 250 to about 2500 nanogram/ml, or from about 250 to about 1000 nanogram/ml.

Epidural or intrathecal administration of an anesthetic may be accomplished via techniques known in the art, such as the use of an intrathecal or epidural catheter. The catheter should be placed closer to the nerves critical for the propagation of any pain sensory information which the practitioner desires to inhibit, without damaging the nerves.

Other routes of administration which are contemplated include: injection, infusion, continuous infusion, localized perfusion bathing target cells directly, via a catheter, via nanoparticle delivery, topical administration (e.g., in a carrier vehicle, a topical control release patch, in a wound dressing, a hydrocolloid, a foam, or a hydrogel), intra-articular, intratumoral, and/or intracranial administration. In certain embodiments, the route of administration is not oral, intravenous, or via inhalation. An appropriate biological carrier or pharmaceutically acceptable excipient may be used. Compounds administered may, in various embodiments, be racemic, isomerically purified, or isomerically pure.

In certain embodiments, anesthetics of the present invention are not administered intravenously. Intravenous administration is often used for general anesthesia (Mathias et al. 2004) and typically results in the rapid distribution of the anesthetic agent throughout the body of a subject. Thus, in certain embodiments, intravenous administration is incompatible for use with regional or local anesthesia.

FIG. 1 provides a flowchart depiction of a general method for delivering a halogenated ether anesthetic. As shown in FIG. 1, method (100) begins with the selection of an halogenated ether compound (102). The halogenated ether anesthetic may be a standard volatile anesthetic gas, or an active agent that is capable or reducing pain and of becoming readily gaseous, as described above.

Solutions

After a halogenated ether anesthetic has been selected, it may be dissolved into a solution (104). The solution may be an aqueous solution, such as saline, artificial cerebrospinal fluid, the subject's own cerebrospinal fluid, or the like. In some variations, other solutions may be appropriate.

Various formulations of saline are known in the art and may be used with the present invention. For example, the saline may be lactated Ringer's solution, acetated Ringer's solution, phosphate buffered saline (PBS), Dulbecco's phosphate buffered saline (D-PBS), Tris-buffered saline (TBS), Hank's balanced salt solution (HBSS), or Standard saline citrate (SSC).

The saline solutions of the present invention are, in certain embodiments, "normal saline" (i.e., a solution of about 0.9% w/v of NaCl). Normal saline has a slightly higher degree of osmolality compared to blood; however, in various embodiments, the saline may be isotonic in the body of a subject such as a human patient. Normal saline (NS) is often used frequently in intravenous drips (IVs) for patients who cannot take fluids orally and have developed severe dehydration. In certain embodiments, "half-normal saline" (i.e., about 0.45% NaCl) or "quarter-normal saline" (i.e., about 0.22% NaCl) may be used with the present invention. Optionally, about 5% dextrose or about 4.5 g/dL of glucose may be included in the saline. In various embodiments, one or more salt, buffer, amino acid and/or antimicrobial agent may be included in the saline.

Various artificial cerebrospinal fluid (ACSF) solutions may be used with the present invention. In certain embodiments, the ACSF is a buffered salt solution (pH 7.4) with the following composition (in mM): NaCl, 120; KCl, 3; $NaHCO_3$, 25; $CaCl_2$, 2.5; $MgCl_2$, 0.5; glucose, 12. ACSF can also be obtained from various commercial sources, such as from Harvard Apparatus (Holliston, Mass.).

In various embodiments, a preservative or stabilizer may be included in the composition or solution. For example, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof. Agents which may be included suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the composition is preferably sterile and must be fluid to facilitate easy injectability. Solutions are preferably stable under the conditions of manufacture and storage and must be preserved against the contaminating action of microorganisms, such as bacteria and fungi. Examples of stabilizers which may be included include buffers, amino acids such as glycine and lysine, carbohydrates such as dextrose, mannose, galactose, fructose, lactose, sucrose, maltose, sorbitol, mannitol, etc. Appropriate stabilizers or preservatives may be selected according to the route of administration desired.

The weight ranges of compounds in the solution may vary. For example, in various embodiments, the composition may comprise about 1-5 wt % anesthetic agent, about 1-5 wt % preservative/stabilizer, about 1-5 wt % NaCl, and about 85%-97% water. The ratio of anesthetic to water may be varied as needed to achieve the desired effect (pain reduction or analgesia, regional anesthesia, etc.).

The solution and/or composition may also be sterilized prior to administration. Methods for sterilization are well known in the art and include heating, boiling, pressurizing, filtering, exposure to a sanitizing chemical (e.g., chlorination followed by dechlorination or removal of chlorine from solution), aeration, autoclaving, and the like.

The active agent gas may be dissolved into the solution in any number of ways. For example, it may be bubbled through the solution, e.g., using a vaporizer, or it may be solubilized by agitation. In certain embodiments, an anesthetic such as a halogenated ether or a volatile anesthetic may be measured in liquid form and directly admixed into a solution. Of course, other suitable methods of dissolving the anesthetic into solution may also be used. After the halogenated ether anesthetic has been solubilized, it may be administered to a subject in need of pain reduction (including pain reduction in the form of anesthesia) epidurally or intrathecally (FIG. 1, 106) using techniques well known in the art. In certain embodiments, a volatile anesthetic is admixed with a solution in a closed vacuum container, and the combined solutions are then mechanically agitated for 3-5 minutes and held in a thermo-neutral sonicator until use.

For intrathecal or epidural applications, oil-in-water emulsions may not be desirable, as a practitioner may not wish to inject oil into the spinal canal. In contrast, saline, artificial CSF, or the patients own CSF may be used for intrathecal or epidural administration of an anesthetic according to the present invention. Certain emulsions of isoflurane have been prepared previously for epidural (da Sila Telles et al., 2004) or intravenous administration (Chai et al., 2006). Lipid emulsions may also pose some risk of infection, as has been observed in the past with bacterially contaminated propofol emulsions. Anesthetic solutions of the present invention which are free or essentially free of a lipid emulsion may thus have a reduced risk of contamination.

In other embodiments, a lipid emulsion or an oil-in-water emulsion may be included in an anesthetic composition of the present invention. For example, an anesthetic composition comprising a volatile anesthetic dissolved in a solution comprising an extractive solvent may also comprise a lipid emulsion or an oil-in-water emulsion. In various embodiments, liposomes (e.g., multilamellar, unilamellar, and/or multivesicular liposomes) or a lipid composition may contain an aqueous solution comprising both a volatile anesthetic an extractive solvent. Inclusion of an oil-in-water emulsion or a lipid emulsion in an anesthetic composition may be used, e.g., to favorably affect the stability of the anesthetic composition and/or alter the pharmacokinetics of the anesthetic. Lipid compositions, lipid emulsions, oil-in-water emulsions, and/or liposomes may be useful, e.g., in nerve block procedures for a regional anesthesia.

Pharmaceutical compositions of the present invention comprise an effective amount of one or more anesthetic or biologically active gas or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one anesthetic or biologically active gas in solution or additional active ingredient will be known to those of skill in the art in light of the present disclosure, as exemplified by Remington: The Science and Practice of Pharmacy, 20th Edition (2000), which is incorporated herein by reference. Moreover, for animal (e.g., human) administration, it will be understood that preparations should meet sterility, pyrogenicity, general safety and purity standards as required by FDA Office of Biological Standards.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example I

Intrathecal Administration of Isoflurane and Sevoflurane

This study was designed to evaluate efficacy of direct intrathecal injection of anesthetic agent gases in reducing pain and providing analgesia. The study was conducted over a one (1) month period using anesthetic gases isoflurane and sevoflurane injected directly intrathecally or dissolved in saline as shown in the studies below. The subject animal used was the rat, since the rat has a well-established model of pain/analgesia testing. In particular, Sprague-Dawley rats weighing over 350 gm were used. The rats were anesthetized with pentobarbital (50 mg/kg), and the anesthetic depth of the animals was determined by corneal reflex and paw withdrawal reflex to a noxious stimulus.

The neck of the rats were shaved and cleaned with disinfectant solutions in order to avoid bacterial contamination during surgery. A midline surgical dissection of the posterior neck muscles was performed to obtain access to the occipito-atlantoid membrane. This membrane was identified and then dissected. A sterile polyethylene catheter was introduced in the subarachnoid space until the lumbar enlargement of the spinal cord (approximately 7-8 cm measured in each animal). The surgical wound was closed, first suturing the neck muscles with 3-0 silk sutures and then closing the skin incision with staples.

After the surgery, the rats were moved to their cages and a radiant lamp was placed over the cages so that the rats would not undergo anesthetic-induced hypothermia. The rats were continuously monitored from the end of the surgery until they were fully awake. Rats showing any motor impairment after surgery were euthanized.

On the fifth day after surgery, those rats without wound infection or motor dysfunction were transported to the pain behavioral lab to enter the intrathecal study with volatile anesthetics. Twelve rats were selected for the study. All these rats had intrathecal catheters. Isoflurane (1-chloro-2,2,2-trifluoroethyl difluoromethyl ether) and sevoflurane (fluoromethyl 2,2,2-trifluoro-1-(trifluoromethyl)ethyl ether) were used as the halogenated ether compounds. Both of these are halogenated volatile anesthetic agents, with isoflurane manufactured by Baxter and sevoflurane manufactured by Abbott Laboratories. The 12 rats were divided into 3 groups of four rats each for study A and B.

In the first group, 2 microliters of preservative-free normal saline was injected via the intrathecal catheter into each rat. This catheter was then flushed with preservative-free normal saline. Pain behavioral testing on this group was then performed.

In the second group, 2 microliters of isoflurane was injected via the intrathecal catheter into each rat. This catheter was also flushed with preservative-free normal saline. This group was then subjected to pain behavioral testing.

In the third group, 2 microliters of sevoflurane was injected via the intrathecal catheter into each rat. This catheter was also flushed with preservative-free normal saline. This group was then subjected to pain behavioral testing.

A "hotplate" behavioral test was used to evaluate pain perception and analgesia. The pain behavioral testing model used in these studies have been well established by Tony Yaksh. (See, e.g. Chaplan et al., 1994; Yaksh et al., 2001; Kim and Chung, 1992; Sorkin et al., 2001). This test involves determining how quickly a rat will withdraw its hind paw in response to a noxious stimulus such as a radiant heat source placed directly underneath its paw. This time for withdrawal is known as "thermal withdrawal latency".

Rats were transferred for testing onto a modified Hargreaves apparatus with a heated glass plate maintained at 25° C. (see Hargreaves et al., 1988). A focused projection bulb below the plate was aimed at the mid-plantar surface of the paw. A photodiode-activated timer measured the withdrawal latency, and a cutoff time of 25 seconds was used to prevent tissue damage. Thermal withdrawal latency to radiant heat was measured at 5 minutes and 30 minutes after each intrathecal injection. Each paw was tested three times, and the results were averaged. The below data was collected for both the right and left hind paws:

TABLE 1

| | Test 1 | | Test 2 | | Test 3 | | |
|---|---|---|---|---|---|---|---|
| | Right | Left | Right | Left | Right | Left | Average |
| Group 1: Control Group (Normal Saline) Tested at 5 minutes ||||||||
| Rat 1: | 9.00 | 9.26 | 10.45 | 6.74 | 8.42 | 9.95 | 8.97 |
| Rat 2: | 11.23 | 9.32 | 6.34 | 7.98 | 10.65 | 8.73 | 7.19 |
| Rat 3: | 7.83 | 8.21 | 9.67 | 11.90 | 8.55 | 6.38 | 8.76 |
| Rat 4: | 9.72 | 8.04 | 6.77 | 8.92 | 7.88 | 8.95 | 8.38 |
| Group 2 Study A: Isoflurane Group Tested at 5 minutes ||||||||
| Rat 5: | 19.81 | 17.23 | 20.38 | 18.91 | 20.34 | 18.82 | 19.25 |
| Rat 6: | 17.19 | 19.24 | 15.88 | 17.65 | 18.59 | 20.72 | 18.21 |
| Rat 7: | 19.20 | 18.11 | 17.90 | 19.80 | 16.71 | 20.07 | 18.63 |
| Rat 8: | 20.31 | 19.71 | 18.34 | 17.18 | 16.75 | 16.38 | 17.95 |
| Group 3 Study B: Sevoflurane Group Tested at 5 minutes ||||||||
| Rat 9: | 13.81 | 14.90 | 13.23 | 15.11 | 16.03 | 14.83 | 14.65 |
| Rat 10: | 17.19 | 13.38 | 14.29 | 12.31 | 13.75 | 12.01 | 13.82 |
| Rat 11: | 14.98 | 12.34 | 13.93 | 11.03 | 12.37 | 14.16 | 13.14 |
| Rat 12: | 10.31 | 11.83 | 13.20 | 12.66 | 17.59 | 12.31 | 12.98 |

Group 1 Average: 8.33 seconds
Group 2 Average: 18.51 seconds
Group 3 Average: 13.65 seconds These rats were then allowed time to recover from their intrathecal injection. There were no apparent adverse effects such as respiratory depression, cardiac, or neurological compromise. At 30 minutes after the injection, the rats were tested again, according to grouping:

TABLE 2

| | Test 1 | | Test 2 | | Test 3 | | |
|---|---|---|---|---|---|---|---|
| | Right | Left | Right | Left | Right | Left | Average |
| Group 1: Control Group (Normal Saline) Tested at 30 minutes ||||||||
| Rat 1: | 7.32 | 8.02 | 9.17 | 8.64 | 5.89 | 7.71 | 7.79 |
| Rat 2: | 6.77 | 5.98 | 7.81 | 6.54 | 9.03 | 8.20 | 8.59 |
| Rat 3: | 7.08 | 8.39 | 7.26 | 8.49 | 9.23 | 9.84 | 8.38 |
| Rat 4: | 8.36 | 9.44 | 9.15 | 9.67 | 8.54 | 7.92 | 8.85 |

TABLE 2-continued

| | Test 1 | | Test 2 | | Test 3 | | |
|---|---|---|---|---|---|---|---|
| | Right | Left | Right | Left | Right | Left | Average |
| Group 2, Study A: Isoflurane Group Tested at 30 minutes ||||||||
| Rat 5: | 9.87 | 9.12 | 10.59 | 9.02 | 8.54 | 9.77 | 9.48 |
| Rat 6: | 9.08 | 6.35 | 7.81 | 8.22 | 10.49 | 11.62 | 8.93 |
| Rat 7: | 6.32 | 8.37 | 9.48 | 8.45 | 11.03 | 10.48 | 10.52 |
| Rat 8: | 9.41 | 10.27 | 6.76 | 7.04 | 7.88 | 10.32 | 9.21 |
| Group 3, Study B: Sevoflurane Group Tested at 30 minutes ||||||||
| Rat 9: | 9.23 | 8.54 | 7.30 | 8.29 | 9.43 | 8.87 | 8.61 |
| Rat 10: | 7.38 | 6.87 | 8.92 | 7.99 | 10.83 | 8.10 | 8.35 |
| Rat 11: | 10.05 | 8.44 | 9.32 | 11.74 | 7.66 | 6.13 | 8.89 |
| Rat 12: | 9.55 | 10.93 | 8.67 | 6.68 | 9.27 | 12.11 | 9.54 |

Group 1 Average: 8.40 seconds
Group 2 Average: 9.53 seconds
Group 3 Average: 8.84 seconds The results of this study demonstrated the efficacy of intrathecal administration of volatile anesthetic agents in reducing pain. At the smallest intrathecally delivered dose of 2 microliters, an analgesic effect of isoflurane and sevoflurane was shown. The thermal latency time was significantly increased, thus showing that the thermal C-fiber pain pathway was effectively dampened. This study also shed some light into the safety of intrathecally delivering active agent gases. None of the rats in the study experienced adverse effects, and all of them fully recovered from the intrathecal injection after 30 minutes, as indicated by the return to thermal latency baseline for all groups.

Example II

Preparation of a 5 µL Sample of Isoflurane Dissolved in Saline

Isoflurane was dissolved into saline using the following method (also referred to as the "bubbling" method). Study C: A mock vaporizing device was created using a 500 ml modified Erlenmeyer flask (2 inlets and 1 catheter into the liquid phase). The flask was partially filled with 0.9% normal saline and a stoppered glass pipette was inserted into the bottom of the liquid phase for injection of isoflurane. A second egress pipette allowed egress of gas from the closed container. 2% isoflurane solution in oxygen at 2 L/min was injected through the pipette, saturating the 0.9% saline solution after approximately 10 minutes of injection. 5 mL was drawn from the saturated saline solution and administered to 10 animals using the procedures outlined in Example I above.

For study C, all animals were prepared as for experiments A and B. The inventors injected 4 animals with 5 microliter of dissolved isoflurane solution (as prepared in 0030) via intrathecal catheter. Note, control (baseline) latency to paw withdrawal is different in Study C due to a different intensity of heat lamp used. Each animal serves as its own control in study C.

Figure 2:
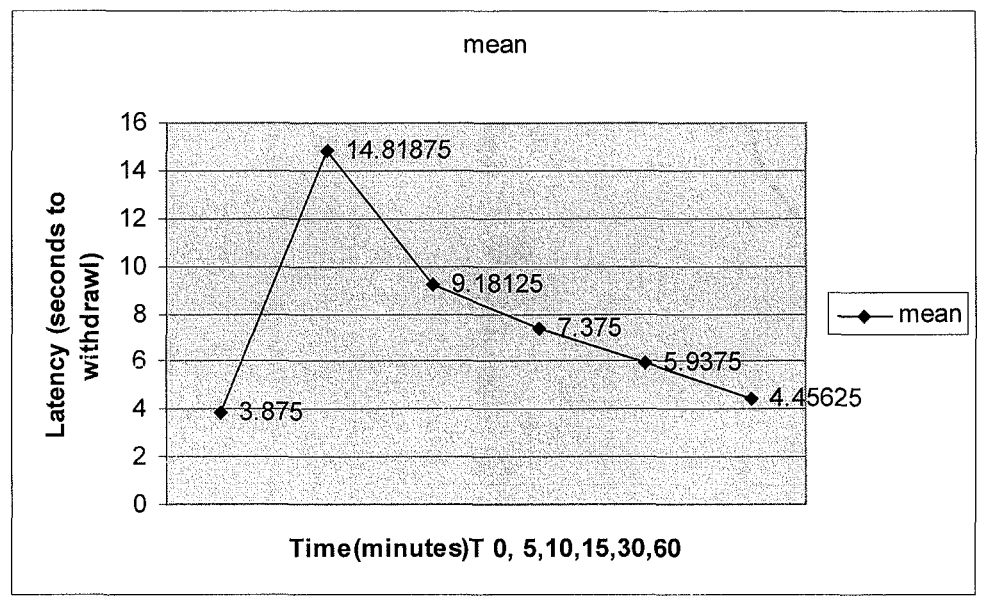
FIG. 2: Inhibition of pain via intrathecal administration of isoflurane solution as measured using the hotplate test.

Study C Data is presented here: in seconds to paw withdrawal to heat source. Table and graphic format. Results are shown in FIG. 2.

TABLE 3

| | CONTROL | 5 MIN | 10 MIN | 15 MIN | 30 MIN | 60 MIN |
|---|---|---|---|---|---|---|
| RAT 1 | 4.8 | 11 | 5.4 | 7.6 | 6.8 | 6.1 |
| | 4.4 | 15 | 9 | 7.3 | 7.2 | 5.8 |
| | 4.8 | 19.5 | 9 | 8.8 | 4.9 | 5.1 |
| | | 20 | 6.8 | 7 | 5.2 | 4.9 |

TABLE 3-continued

|       | CONTROL  | 5 MIN    | 10 MIN  | 15 MIN   | 30 MIN   | 60 MIN   |
|-------|----------|----------|---------|----------|----------|----------|
| RAT 2 | 3.4      | 10.9     | 9.9     | 10.4     | 8.2      | 3.8      |
|       | 4.3      | 12.6     | 8.7     | 9.4      | 6.9      | 4.7      |
|       | 3.6      | 18.1     | 12      | 5.4      | 8.1      | 7        |
|       |          | 17.3     | 9       | 13.4     | 6.4      | 4.1      |
| RAT 3 | 3.6      | 14.2     | 12.2    | 6.1      | 5.2      | 4.2      |
|       | 3.8      | 20       | 12      | 7.1      | 6.1      | 3.5      |
|       | 4.7      | 20       | 9.1     | 4.8      | 5.8      | 3.3      |
|       |          | 16       | 8.9     | 5.2      | 6.5      | 3.8      |
| RAT 5 | 3.9      | 9.8      | 8.8     | 7.9      | 4.9      | 4.2      |
|       | 2.6      | 11.8     | 7.8     | 6.4      | 4.3      | 3.5      |
|       | 2.6      | 9.1      | 10.2    | 6.9      | 4.7      | 3.8      |
|       |          | 11.8     | 8.1     | 4.3      | 3.8      | 3.5      |
| Mean  | 3.875    | 14.81875 | 9.18125 | 7.375    | 5.9375   | 4.45625  |
| SD    | 0.767671 | 3.809235 | 1.77067 | 2.231171 | 1.266331 | 1.073293 |

Example III

Intrathecal Inhibition of Pain Using Isoflurane Dissolved in Artificial Cerebrospinal Fluid Pain sensitivity was measured after intrathecal administration of isoflurane in artificial cerebrospinal fluid (ACSF). Further, as detailed below, the isoflurane was first dissolved in ACSF and then sonicated before administration. The dose response relationship was then evaluated by generating a stimulus-response (SR) graph in order to determine relevant concentrations of isoflurane that may be administered intrathecally to achieve analgesia or anesthesia. The characterization of the pharmacological profile of intrathecal administration of isoflurane in ACSF was performed in this example using rats; further, as would be appreciated by one of skill in the art, analogous approaches may be used to determine the precise pharmacological profile in humans.

Isoflurane dissolved in ACSF was prepared by the following method. Isoflurane was admixed in a closed vacuum container in a v/v ratio of 10-50% with buffered salt solution that approximates cerebrospinal fluid (pH 7.4) with the following composition (in mM): NaCl, 120; KCl, 3; NaHCO$_3$, 25; CaCl$_2$, 2.5; MgCl$_2$, 0.5; glucose, 12. The combined solutions were mechanically agitated for 3-5 min and then held in a thermo-neutral sonicator until use.

The solutions of isoflurane in ACSF were then administered to rats intrathecally via the following method. Treatment solution is delivered via intrathecal catheter that overlies lumbar segment L1-2 in a volume of 10 µl followed by a 10 µl flush of ACSF.

Pain perception was tested after intrathecal administration of isoflurane dissolved in artificial CSF using the "hotplate" behavioral test, as described above, with the modification that a cutoff time of 20 seconds was used. As stated above the "hotplate" behavioral test involves testing the hind paw withdrawal threshold to radiant heat (i.e., duration of time between before a rat to lifts a paw away from a heat source).

Figure 3:
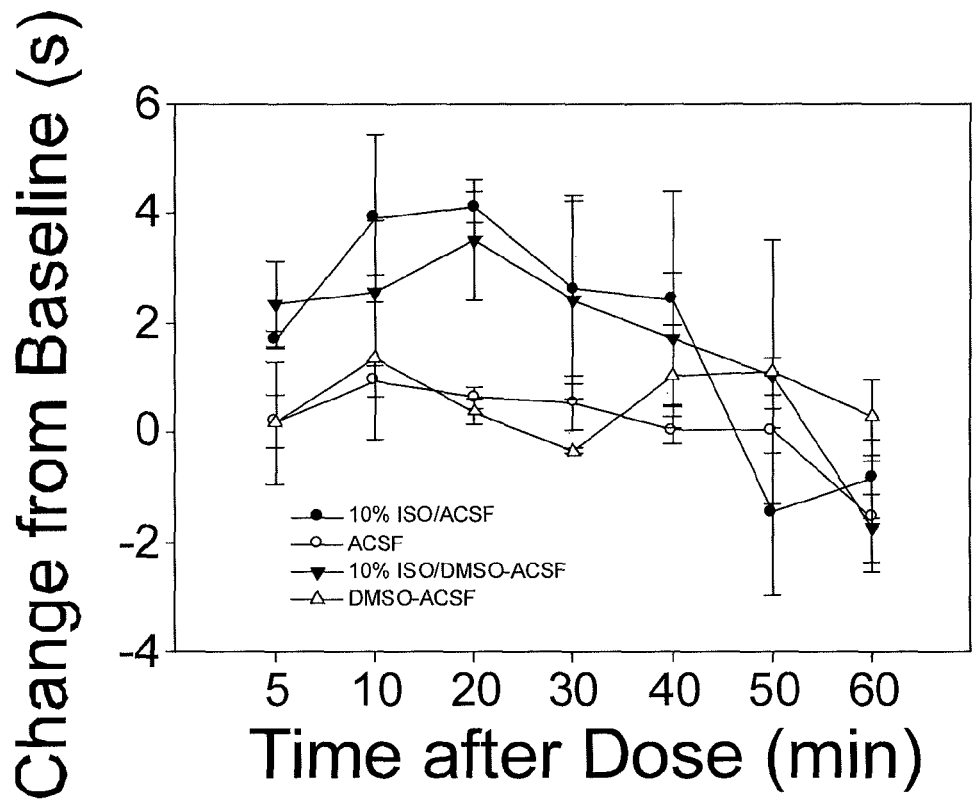
FIG. 3: Inhibition of pain using intrathecal isoflurane in artificial cerebrospinal fluid (ACSF) and/or DMSO. The time course for Isoflurane-ACSF and Isoflurane-DMSO/ACSF, at a dose of 1.46 mg isoflurane, is shown.

Intrathecal administration of isoflurane in ACSF resulted in analgesia. As shown in FIG. 3, intrathecal administration of isoflurane in ACSF (i.e., at a 1.46 mg dose of isoflurane) resulted in analgesia as measured by testing the hind paw withdrawal threshold to radiant heat. A 10 µL solution of isoflurane in ACSF (10% v/v) was used. As described below, this dose of isoflurane represents a moderate dose of intrathecal isoflurane. Further, as shown in FIG. 3, DMSO may be included in the pharmaceutical composition for intrathecal injection. A concentration of 1% DMSO was used.

Figure 4:
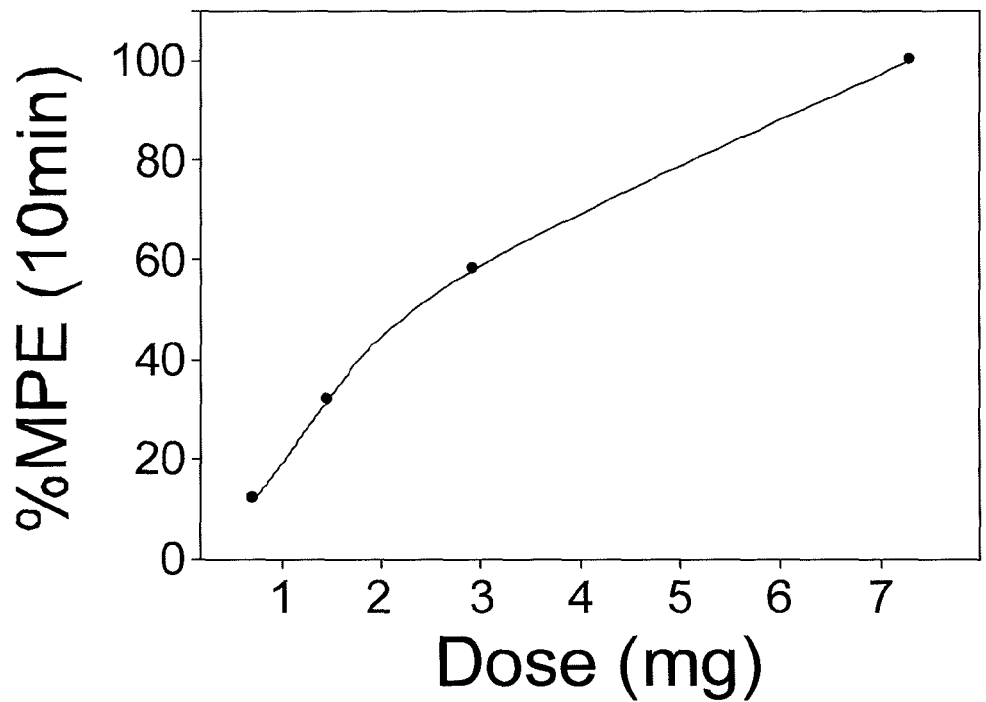
FIG. 4: A stimulus response (SR) graph is shown of the maximal possible effect (MPE) by dose for the time point of 10 minutes after intrathecal injection of isoflurane-ACSF.

The dose response relationship was then evaluated by generating a stimulus-response (SR) graph in order to standardize responses across animals and determine relevant concentrations of isoflurane that may be administered intrathecally to achieve analgesia or anesthesia. FIG. 4 shows an stimulus-response (SR) graph of the maximal possible effect (MPE) by dose for the time point of 10 minutes after the injection of isoflurane in ACSF. Various doses of isoflurane are shown on the x-axis; for example, the 10% v/v solution of isoflurane used above, as shown in FIG. 3, corresponds to approximately a 34% MPE as shown in FIG. 4. Pharmaceutical compositions including ACSF and/or DMSO are shown in FIG. 3. MPE is used here to standardize responses across animals. MPE is calculated as ((drug response time-baseline response time)/(cutoff time-baseline response time))*100. The cutoff time used here was 20 seconds. As shown in FIG. 4, a substantial analgesic effect was observed. A 1% DMSO solution was used for the data shown in FIG. 4.

Example IV

Preparation of Anesthetic Compositions Comprising an Extractive Solvent

The following solutions were prepared. Isoflurane was obtained. NMP was obtained from Sigma-Aldrich Chemical company. A 40% (v/v) solution isoflurane-NMP solution was made adding 40 ml of isoflurane to 60 ml of NMP. A 40% (v/v) solution isoflurane-ethanol solution was made adding 40 ml of isoflurane to 60 ml of ethanol.

Saline compositions with varying concentrations of isoflurane and NMP were made by mixing the above NMP-isoflurane solution with saline as follows:

TABLE 4

| Sample | Saline (ml) | Base-Isoflurane Compositions(ml) | % Isoflurane | % NMP |
|--------|-------------|----------------------------------|--------------|-------|
| A      | 0           | 10                               | 40%          | 60%   |
| B      | 2           | 8                                | 32           | 48    |
| C      | 4           | 6                                | 24           | 36    |
| D      | 5           | 5                                | 20           | 30    |
| E      | 6           | 4                                | 16           | 24    |
| F      | 8           | 2                                | 8            | 12    |
| G      | 10          | 0                                | 0            | 0     |

Control compositions with varying concentrations of isoflurane-ethanol were made by mixing the above isoflurane-ethanol compositions with saline as follows:

TABLE 5

| Sample | Saline (ml) | Control-Isoflurane Compositions(ml) | % Isoflurane | % Ethanol |
|---|---|---|---|---|
| H | 0 | 10 | 40% | 60% |
| I | 2 | 8 | 32 | 48 |
| J | 4 | 6 | 24 | 36 |

TABLE 5-continued

| Sample | Saline (ml) | Control-Isoflurane Compositions(ml) | % Isoflurane | % Ethanol |
|---|---|---|---|---|
| K | 5 | 5 | 20 | 30 |
| L | 6 | 4 | 16 | 24 |
| N | 8 | 2 | 8 | 12 |
| M | 10 | 0 | 0 | 0 |

To determine the stability of the compositions, the following experiment may be performed. Each sample is divided into two containers containing 5 mls of the sample. One of the samples is capped. The other sample is left uncapped. Over time (1 hour, 6 hour, 24 hour, etc.), the samples are examined to see if the isoflurane has separated from solution. Furthermore, the concentration of isoflurane in each solution may be determined at each time point. The uncapped sample may be compared to the capped sample to determine the stability of the solution. Furthermore, the isoflurane-NMP compositions may then be compared to the control compositions. It is anticipated that the anesthetic compositions will remain miscible at all concentrations.

Example V

Preparation of Isoflurane Compositions and Stability Testing

The stability of isoflurane in the compositions was determined in two ways. Firstly, the compositions were examined for the presence of phase separation at the macroscopic level. Secondly, isoflurane content of the compositions were determined by weighing the remaining isoflurane in the composition when they were left uncapped over time. Briefly, glass vials were filled with 5-10 ml of the composition vehicle and then weighed; one of them did not receive isoflurane and served as control. The other vials received varying amounts of isoflurane. They were left uncapped in the hood. Over time (0, 0.4, 1, 16, 24 h), the vials were weighed to see if the isoflurane stayed in the composition or evaporated. The amount evaporated over time in the vehicle was subtracted from that in the isoflurane composition, and therefore the amount of isoflurane in the vehicle was roughly determined at each time point.

Pure form of isoflurane is a volatile agent. In order to determine the volatility of isoflurane, two vials received the indicated amounts of pure form of isoflurane. The vials were placed in the chemical fume hood and left uncapped. The vials were weighed in the indicated times to determine the amount of evaporated isoflurane. As it is shown in the table below 0.7893 g isoflurane was evaporated within 3 hrs whereas 3.4825 g isoflurane took approximately 8 hrs to evaporate completely. These amounts of isoflurane are similar to the amounts of isoflurane that were used to prepare isoflurane (iso) compositions as shown below.

TABLE 6

| Pure form of Isoflurane (g) | 0 h (% remaining iso) | 0.25 h (% remaining iso) | 1 h (% remaining iso) | 2 h (% remaining iso) | 3 h (% remaining iso) | 5 h (% remaining iso) | 7 h | 8 h |
|---|---|---|---|---|---|---|---|---|
| 0.7893 | 100 | 85 | 52 | 14 | 0 | | | |
| 3.4825 | 100 | 96 | 86 | 75 | 62 | 38 | 13 | 3 |

Preparation of isoflurane solution (v/v) in N-methyl-2-pyrrolidone (NMP): Pure isoflurane USP (Forane) liquid is mixed with NMP (Sigma-Aldrich) in the indicated concentrations; the mixture was vortexed vigorously to prepare homogenous isoflurane-NMP solution. In order to reduce the amount of NMP in the solution, saline (0.9% NaCl) was added to the mixture.

TABLE 7

| | NMP (%) | Saline (%) | Isoflurane (%) | Appearance of solutions |
|---|---|---|---|---|
| 1 | 90 | — | 10 | Clear |
| 2 | 60 | — | 40 | Clear |
| 3 | 63 | 27 | 10 | Clear |
| 4 | 72 | 20 | 8 | Clear |

TABLE 8

| Isoflurane concentration in NMP | 0 h (% remaining iso) | 0.25 h (% remaining iso) | 1 h (% remaining iso) | 16 h (% remaining iso) | 24 h (% remaining iso) |
|---|---|---|---|---|---|
| 10 | 100 | 99 | 99 | 94 | 91 |
| 30 | 100 | 99 | 98 | 90 | 86 |

As it is shown in Table 7, 10% and 40% of isoflurane was mixed with NMP, and the resulting solution looked clear. 10% isoflurane in NMP could mix with saline until NMP concentration was 63% minimum, meaning that when NMP concentration was less than 63% in the solution, isoflurane precipitated. As it is shown in table 3, NMP reduced the volatility of isoflurane (Table 8 versus Table 6).

Preparation of Isoflurane Solution (v/v) in Propylene Glycol:

Pure isoflurane USP (Forane) liquid was mixed with Propylene Glycol (Sigma-Aldrich) in the indicated concentrations; the mixture was vortexed vigorously to prepare homogenous isoflurane-Propylene Glycol solution.

TABLE 9

| | Propylene Glycol (%) | Saline (%) | Isoflurane (%) | Appearance of solutions |
|---|---|---|---|---|
| 1 | 90 | — | 10 | Clear |
| 2 | 70 | — | 30 | Clear |
| 3 | 72 | 20 | 8 | Clear |

TABLE 10

| Isoflurane concentration in Propylene Glycol | 0 h (% remaining iso) | 0.25 h (% remaining iso) | 1 h (% remaining iso) | 16 h (% remaining iso) | 24 h (% remaining iso) |
|---|---|---|---|---|---|
| 10 | 100 | 89 | 86 | 44 | 23 |
| 30 | 100 | 94 | 90 | 53 | 35 |

As it is shown in Table 9, 10% and 30% of isoflurane was mixed with propylene glycol, and the resulting solution looked clear. 10% isoflurane in propylene glycol could mix with saline until propylene glycol concentration was 72% minimum. As it is shown in table 10, propylene glycol reduced the volatility of isoflurane (Table 10 versus Table 6), however it was not as good as NMP (Table 10 versus Table 8).

Preparation of Isoflurane Solution (v/v) in Dimethylsulfoxide (DMSO):

Pure isoflurane USP (Forane) liquid is mixed with DMSO (BDH) in the indicated concentrations; the mixture was vortexed vigorously to prepare homogenous isoflurane-DMSO solution. In order to prepare isoflurane solutions with smaller amounts of DMSO in the solution, saline (0.9% NaCl) was added to the mixture.

TABLE 11

| | DMSO (%) | Saline (%) | Isoflurane (%) | Appearance of solutions |
|---|---|---|---|---|
| 1 | 90 | — | 10 | Clear |
| 2 | 50 | — | 50 | Clear |
| 3 | 72 | 20 | 8 | Clear |

As it is shown in Table 11, 10% and 50% of isoflurane was mixed with DMSO, and the resulting solution looked clear. 8% isoflurane in the combination of 72% DMSO and 20% saline was prepared, and the resulting solution looked clear.

Animal Testing

Intraplanar Administration of Isoflurane:

100 µl of pure form Isoflurane or 100 µl of 2% Lidocaine was injected subcutaneously into the planar surface of the hindpaw. Every rat, the contralateral hindpaw, served as its own control.

Measurement of Paw Withdrawal Latency:

Rats are tested for response to thermal stimulation using radiant heat (Planar Analgesia Instrument, UgoBasile, Italy). After the rats acclimate for 15 min under the acrylic boxes that allow minimal movement, the heat source was positioned beneath the mid-plantar surface of the hind paw. Withdrawal latency is defined as the period of time from the beginning of the thermal stimulation to the brisk withdrawal of the hind paw. To avoid tissue damage, a cutoff time of 22 s was set. Thermal stimulation was applied three times to each hind paw at an inter-stimulus interval of 3-5 min. Thermalnociceptive threshold was assessed before and after the treatment. An increase in the withdrawal threshold in the treated paw compared to the control paw is assessed as analgesic activity of the tested formulation.

Statistical Analysis:

For statistical comparison, student paired t-test analysis was used. Differences were considered significant at $P<0.05$.

Figure 5:
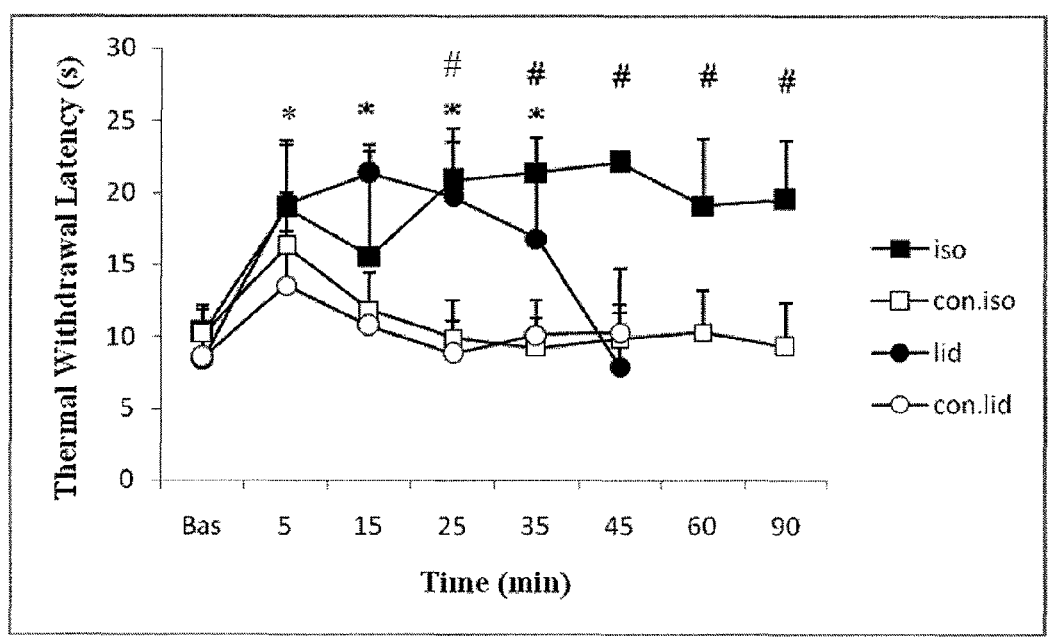
FIG. 5: Inhibition of pain using a Plantar Heat Stimulation Test via local administration of isoflurane. The administration of isoflurane into the hindpaw produced a significant antinociceptive effect (iso) when compared to the untreated paw (con.iso). The antinociceptive effect started at 25 min and continued throughout the experiment. The administration of lidocaine (lid versus con.lid) resulted in significant antinociceptive effect, which started at 5 min, peaked at 15 min and returned to the baseline levels at 45 min. #$P<0.05$ isoflurane versus control (n=4). * $P<0.05$ lidocaine versus control (n=3).

Experiments were performed as described above. As shown in FIG. 5, the administration of isoflurane into the hindpaw produced a significant ($P<0.05$) antinociceptive effect (iso) when compared to the untreated paw (con.iso). The antinociceptive effect started at 25 min and continued throughout the experiment. The administration of lidocaine (lid versus con.lid) resulted in significant antinociceptive effect, which started at 5 min, peaked at 15 min and returned to the baseline levels at 45 min.

Example VI

Topical Application of Isoflurane for Analgesia in Humans

To evaluate the efficacy of topical isoflurane, a small amount of (1 cc) of 50% ISO/DMSO solution was applied to the skin of a human subject. The subject observed local anesthetic properties where the 50% ISO/DMSO solution was applied with a notable local anesthetic response to light touch for approximately one hour duration. No skin irritation was observed.

To further quantify this local anesthetic response in human subjects, clinical studies may be performed as described below. Isoflurane (ISO) is a widely used volatile anesthetic agent with a well established safety profile. Dimethyl sulfoxide (DMSO) is an organic solvent which has been used as a drug delivery system to facilitate drug movement across the stratum corneum (the water impermeable skin layer). Previous work had shown local anesthesia with lecithin-coated microdroplets of methoxyflurane (Haynes et al. 1991).

The following approach may be used to test the analgesia of topical isoflurane. Studies similar to those involving topical amitryptiline studies (clinicaltrials.gov/show/NCT00471445) may be performed. Cutaneous evaluation in human volunteers for efficacy and or local skin irritation may also be tested. In the example of amitryptiline, important advances came through pilot human trials with volunteers comparing different doses and vehicle alone for skin irritation and pain blocking properties (Gerner et al. 2003) To differentiate between vehicle and active drug, several sites will be tested as outlined below to include a vehicle only site versus drug+vehicle (in different doses).

Subject Eligibility:

Test subjects should be volunteer adults without health problems including lack of skin sensitivity or other medical problems. They need to be literate and agree to an application of test medications to their forearm with a subsequent testing protocol for 4 hours.

Treatment Plan:

Healthy volunteers may have 3 circles approximately 10 cm in diameter drawn on their nondominant forearm with a marking pen. Baseline vital signs may be taken.

Medication may be applied as follows: Low dose ISO/High dose ISO/Vehicle only to the three spots respectively and covered with a tegaderm (6×7 cm, 3M Healthcare, St Paul Minn.). This may be removed after 15 minutes.

Testing may be done at the center of the three circles at baseline (pre-application), 15 minutes (after dressing removal), 60 minutes, 3 hours, and 24 hours. Testing may include sensitivity to light touch with:

Touch Detection Thresholds. (a Delta-Small Myelinated Fibers-"Fast Pain"Touch):

Touch detection thresholds may be determined using the up/down method of Dixon 1 with 6 von Frey monofilaments that are calibrated to administer a force of 0.1, 0.5, 0.9, 3.2, 6.1 or 8.0 mN. Starting with 0.5 mN, the von Frey monofilament may be applied for approximately 1 sec. If the subject fails to detect the stimulus, then the next higher force von Frey monofilament is applied. When the subject detects the presence of the stimulus, the next lower von Frey is administered. The up/down test sequence continues for four additional von Frey applications after the initial detection. The 50% mechanical detection threshold is calculated using the procedure described in Dixon 1. If there is no detection to the highest force von Frey monofilament, then the 50% detection threshold is assigned the value of 19 mN;

Pain Detection (C Fiber-Large Unmyelinated "Slow Pain"), Sharpness Threshold and Pain to Needle Probes:

Sharpness detection may be determined using a weighted needle device 2. The tip of 30 gauge needle (200 im diameter) is filed to produce a flat, cylindrical end. A cotton tip applicator is inserted into the Luer connection of the needle, and washers were placed on the shaft of the cotton tip applicator to achieve the desired force level for the stimulus. The entire assembly is then placed inside a 30 cc syringe so that the needle came out of the tip of the syringe and the assembly moved freely within the syringe. When the needle is applied to the skin surface, a reliable and consistent force is applied. Three forces will be used: 100, 200 and 400 mN. Each stimulus is applied for about 1 sec. Each force is applied 10 times within each area of interest in a pseudo-random order. The subjects are instructed to indicate if the stimulus is sharp. If a stimulus is sharp, the subject then indicates if the stimulus is painful.

To assess for skin irritation, the subjects may be asked to rate the "local skin irritation" at each location at each time point on a 0-10 scale (0=not irritated at all and 10=extremely irritated). Finally, the skin may be examined for redness and obvious irritation at the site at each time point as a "present or absent."

The disclosures of each and every patent, patent application, and publication cited herein are hereby incorporated herein by reference in their entirety.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

REFERENCES

The following references, to the extent that they provide exemplary procedural or other details supplementary to those set forth herein, are specifically incorporated herein by reference.

U.S. Pat. No. 5,336,429.
Chaplan et al., *J. Neurosci. Methods*, 53:55-63, 1994.
Chai Y. F. et al. *Anesthesiology* 105: A743, 2006.
da Sila Telles Mathias L, et al., *Rev. Bras. Anaestesiol Campianas* 54(5), 2004.
Digger T et al. *Hospital Pharmacists* 10: 432, 2003.
Fassoulaki et al. *Can J Anaesth* 45(12): 1151-1155, 1998.
Gerner P, et al. *Reg Anesth Pain Med.* 28(4):289-93, 2003.
Hargreaves et al., *Pain,* 32:77-88, 1988.
Haynes and Kirkpatrick *Reg Anesth,* 16(3):173-80, 1991.
Kim and Chung, *Pain,* 50:355-363, 1992.
Mathias et al., *Revista Brasileira de Anestesiologia*, ISSN 0034-7094, 2004.
Moller et al., *Lancet.,* 351:857-861, 1998.
Rasmussen et al., *Acta Anaesthesiologica Scandinavica,* 47(3):260-266, 2003.
Remington: *The Science and Practice of Pharmacy,* 20$^{th}$ Ed., Baltimore, Md.: Lippincott Williams & Wilkins, 2000
Rogers et al., *BMJ,* 321:1-12, 2000.
Sorkin et al., *Anesthesiology,* 95:965-973, 2001.
Yaksh et al., *J. Appl. Physiol.,* 90:2386-2402, 2001.

The invention claimed is:

1. A method for reducing pain in a subject in need of such pain reduction, the method consisting of transdermally or topically administering to the subject a pharmacologically acceptable solution consisting of a volatile anesthetic dissolved therein in an amount effective to reduce pain and an extractive solvent in an amount effective to reduce volatility of the volatile anesthetic,
   wherein the volatile anesthetic is at least one selected from the group consisting of isoflurane, halothane, enflurane, sevoflurane, desflurane, and methoxyflurane;
   wherein the extractive solvent is at least one selected from the group consisting of dimethyl sulfoxide (DMSO), dimethylformamide, dimethylacetamide, N-methyl-2-pyrrolidone (NMP), dimethylisosorbide, ethanol, propanol and isopropanol; and
   wherein said topical or transdermal administration of the volatile anesthetic reduces pain in the subject.

2. The method of claim 1, wherein the extractive solvent comprises from about 10% to about 75% of the solution.

3. The method of claim 2, wherein the extractive solvent comprises from about 10% to about 25% of the solution.

4. The method of claim 2, wherein the extractive solvent comprises from about 25% to about 75% of the solution.

5. The method of claim 1, wherein the pain is chronic pain.

6. The method of claim 1, wherein the pain is acute pain.

7. The method of claim 1, wherein the anesthetic is delivered to anesthetize a portion of the subject prior to a surgery, during a surgery, or after a surgery.

8. The method of claim 1, wherein the volatile anesthetic is isoflurane.

9. The method of claim 1, wherein the volatile anesthetic is sevoflurane.

10. The method of claim 1, wherein the volatile anesthetic is methoxyflurane.

11. The method of claim 1, wherein the solution comprises from about 1% to about 99% v/v anesthetic in solution.

12. The method of claim 11, wherein the solution comprises from about 10% to about 75% v/v anesthetic in solution.

13. The method of claim 11, wherein the anesthetic is isoflurane.

14. The method of claim 11, wherein the solution comprises about 75%-99% anesthetic in solution.

15. The method of claim 1, wherein the delivery of the volatile anesthetic is continuous.

16. The method of claim 15, wherein the continuous delivery is achieved via an infusion pump.

17. The method of claim 1, wherein the delivery of the volatile anesthetic is periodic.

18. The method of claim 1, wherein the delivery of the volatile anesthetic is a one-time event.

19. The method of claim 1, wherein the delivery of the volatile anesthetic is both periodically administered and continuously administered to the subject on separate occasions.

20. The method of claim 1, wherein the reduction comprises elimination of pain perception of a portion of the body of the subject.

21. The method of claim 1, wherein the pharmacologically acceptable solution is sterile.

22. The method of claim 1, wherein the subject is a human.

23. The method of claim 1, wherein the subject is a mouse or a rat.

24. The method of claim 1, wherein the extractive solvent is DMSO, and the volatile anesthetic is isoflurane.

25. The method of claim 24, wherein the DMSO comprises from about 10% to about 50% of the solution.

26. The method of claim 1, wherein the pain reduction is achieved with substantially no inhibition of motor function in the subject.

27. The method of claim 1, wherein the volatile anesthetic is administered more than once and timed to achieve pain reduction with substantially no inhibition of motor function in the subject.

* * * * *

UNITED STATES PATENT AND TRADEMARK OFFICE
CERTIFICATE OF CORRECTION

PATENT NO.       : 9,675,544 B2                                              Page 1 of 1
APPLICATION NO. : 12/863755
DATED            : June 13, 2017
INVENTOR(S)      : Capelli et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 654 days.

Signed and Sealed this
Twenty-fifth Day of September, 2018

Andrei Iancu
*Director of the United States Patent and Trademark Office*